United States Patent
Li et al.

(10) Patent No.: US 10,364,234 B2
(45) Date of Patent: Jul. 30, 2019

(54) PYRIDINECARBOXAMIDE DERIVATIVES, PREPARATION METHOD THEREOF AND PHARMACEUTICAL USES THEREOF

(71) Applicants: Jiangsu Hengrui Medicine Co., Ltd., Lianyungang, Jiangsu (CN); Shanghai Hengrui Pharmaceutical Co., Ltd., Shanghai (CN)

(72) Inventors: Xin Li, Shanghai (CN); Qing Dong, Shanghai (CN); Piaoyang Sun, Jiangsu (CN)

(73) Assignees: Jiangsu Hengrui Medicine Co., Ltd., Lianyungang, Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 15/531,525

(22) PCT Filed: Nov. 10, 2015

(86) PCT No.: PCT/CN2015/094164
§ 371 (c)(1),
(2) Date: May 30, 2017

(87) PCT Pub. No.: WO2016/091042
PCT Pub. Date: Jun. 16, 2016

(65) Prior Publication Data
US 2017/0342059 A1    Nov. 30, 2017

(30) Foreign Application Priority Data
Dec. 8, 2014  (CN) .......................... 2014 1 0741280

(51) Int. Cl.
C07D 405/14    (2006.01)
A61K 31/4545   (2006.01)
C07D 401/12    (2006.01)

(52) U.S. Cl.
CPC ........ C07D 405/14 (2013.01); A61K 31/4545 (2013.01); C07D 401/12 (2013.01)

(58) Field of Classification Search
CPC .................................................. C07D 405/14
USPC .................................. 546/193, 194; 514/318
See application file for complete search history.

(56) References Cited

U.S. PATENT DOCUMENTS 8,673,920 B2 * 3/2014 Pasternak .......... C07D 295/135
                                                        514/218

FOREIGN PATENT DOCUMENTS

| WO | 2010129379 A1 | 11/2010 |
|---|---|---|
| WO | 2012058116 A1 | 5/2012 |
| WO | 2012058134 A1 | 5/2012 |
| WO | 2013028474 A1 | 2/2013 |
| WO | 2013039802 A1 | 3/2013 |
| WO | 2013062892 A1 | 5/2013 |
| WO | 2013066714 A1 | 5/2013 |
| WO | 2014015495 A1 | 1/2014 |
| WO | 2014018764 A1 | 1/2014 |
| WO | 2014085210 A1 | 6/2014 |

OTHER PUBLICATIONS

Bundgaard, Design of Prodrugs, Chapter 1, p. 1. (Year: 1985).*
Silverman, Prodrugs and Drug Delivery Systems, The Organic chemistry of Drug Design and Drug action, Chapter 8, pp. 352-400. (Year: 1992).*
Banker et al., Prodrugs, Modern Pharmaceutics, 3 rd edition, Revised and Expanded, pp. 451 and 596. (Year: 1986).*
Jordan, "Tamoxifen . . . " Nature Rev. v.2, p. 205-213. (Year: 2003).*
Ettmayer et al., "Lessons Learned from Marketed and Investigational Prodrugs", J. Med. Chem., 47(10): 2393-2404. (Year: 2004).*
Stella, Valentino, "Prodrugs as therapeutics", Expert Opin. Ther. Patents. 14(3): 277-280. (Year: 2004).*
Testa, "Prodrug researchL futile or fertile?" Biochemical Pharmacology, 868,: 2097-2106. (Year: 2004).*
Balant ed in Wolff et al., Burger's Medicinal Chemistry and Drug Discovery, 5th ed. vol. 1: Principles and Practice, pp. 949-982. (Year: 1996).*
Int'l Search Report dated Feb. 18, 2016 in Int'l Application No. PCT/CN2015/094164.

* cited by examiner

*Primary Examiner* — Patricia L Morris
(74) *Attorney, Agent, or Firm* — Panitch Schwarze Belisario & Nadel LLP

(57) ABSTRACT

Pyridinecarboxamide derivatives, preparation methods, and a pharmaceutical uses thereof are provided. In particular, pyridinecarboxamide derivatives represented by general formula (I), wherein the substituents of the formula (I) are defined in the specification are provided. Also provided are a preparation method for the pyridinecarboxamide derivatives of formula (I), a pharmaceutical composition containing the pyridinecarboxamide derivatives, and uses of the pyridinecarboxamide derivatives as therapeutic agents, especially as inhibitors of the Renal Outer Medullary Potassium channel (ROMK) and in the preparation of medicaments for treating and/or preventing hypertension and heart failure.

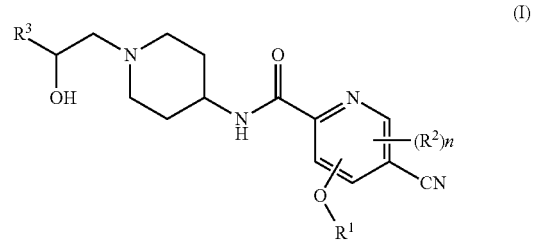

16 Claims, 3 Drawing Sheets

PYRIDINECARBOXAMIDE DERIVATIVES, PREPARATION METHOD THEREOF AND PHARMACEUTICAL USES THEREOF

CROSS-REFERENCE TO RELATED APPLICATION

This application is a Section 371 of International Application No. PCT/CN2015/094164, filed Nov. 10, 2015, which was published in the Chinese language on Jun. 16, 2016, under International Publication No. WO 2016/091042 A1, and the disclosure of which is incorporated herein by reference.

FIELD OF THE INVENTION

The present invention relates to pyridinecarboxamide derivatives, a preparation method thereof and a pharmaceutical composition containing the same, as well as their use as therapeutic agents, especially as inhibitors of the Renal Outer Medullary Potassium channel (ROMK), and in the preparation of medicaments for the treatment and/or prevention of disorders resulting from excessive salt and water retention, including hypertension and heart failure.

BACKGROUND OF THE INVENTION

Increasing renal salt reabsorption can cause a risk of hypertension. On the contrary, inhibition of renal reabsorption function can promote the excretion of urine, which results in diuretic and antihypertensive effects. Common diuretics are thiazide diuretics, which are first-line antihypertensive drugs in USA that primarily act on sodium-chloride ($Na^+$—$Cl^-$) transporters. The Loop diuretics are more effective for patients with impaired renal function, and they play a role through sodium-potassium-chloride ($Na^+$—$K^+$-$2Cl^-$)— transfer proteins. However, both drugs can cause hypokalemia (symptoms: weakness, fatigue, muscle cramps, constipation, and heart rhythm problems, such as arrhythmia), which increases the risk of morbidity and mortality of cardiovascular disease.

Renal Outer Medullary Potassium channel (ROMK) is also known as the inward-rectifying potassium channel 1.1 (Kir1.1). The ROMK channel, cooperating with the Na+-K+-2Cl— co-transfer protein NKCC2 (responsible for NaCl transport) through the apical membrane conductance of the renal thick ascending limb (TAL), can regulate the reabsorption of potassium. The ROMK was found to be directly associated with the renal secretory channel. When the ROMK gene is knocked out in mice, there is a loss of TAL and CCD 35-pS ion channels as well as a loss of the other K+ channels. Batter syndrome is an autosomal recessive disease characterized by massive loss of salt in the kidneys, hypokalemia, and low blood pressure. Batter syndrome is mainly caused by mutations in the ROMK or Na+-K+-2Cl— co-transfer proteins. The difference is that the hypokalemia of the batter syndrome caused by the mutation of ROMK is much milder compared to that caused by the mutation of Na+-K+-2Cl— co-transfer proteins. In summary, inhibition of ROMK function can effectively inhibit the salt reabsorption function of Na+-K+-2Cl— co-transfer proteins and promote the excretion of urine, thereby resulting in diuretic and antihypertensive effects, without causing hypokalemia. Although a number of ROMK inhibitors have been disclosed at present, such as in PCT Patent Application Publications WO2010129379, WO2012058134, WO2012058116, WO2012058134, WO2013066714, WO2013028474, WO2014085210, WO2014018764, WO2014015495, WO2014085210, WO2013039802, WO2013062892 and WO2012058116, more compounds with better hERG selectivity need to be developed. The present invention provides a series of novel compounds represented by general formula (I), wherein a polar group is added, which can reduce ClogP, enhance the hERG selectivity and are much safer, while maintaining the ROMK inhibitory activity.

SUMMARY OF THE INVENTION

The present invention is directed to a compound of formula (I),

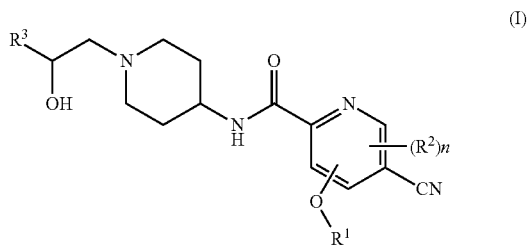

(I)

or a tautomer, mesomer, racemate, enantiomer, diastereomer, or mixture thereof, or pharmaceutically acceptable salt thereof,
wherein
$R^1$ is alkyl, wherein the alkyl is optionally further substituted by one or more groups selected from the group consisting of halogen, hydroxyl, alkoxy, cycloalkyl, heterocyclyl, aryl, heteroaryl, carboxyl and carboxylic ester;
$R^2$ is selected from the group consisting of hydrogen, alkyl, halogen, cyano, nitro, alkoxy, cycloalkyl and heterocyclyl, wherein the alkyl, alkoxy, cycloalkyl or heterocyclyl is optionally further substituted by one or more groups selected from the group consisting of alkyl, halogen, hydroxyl, hydroxyalkyl, alkoxy, cycloalkyl, heterocyclyl, aryl, heteroaryl, carboxyl and carboxylic ester;
$R^3$ is selected from the following groups:

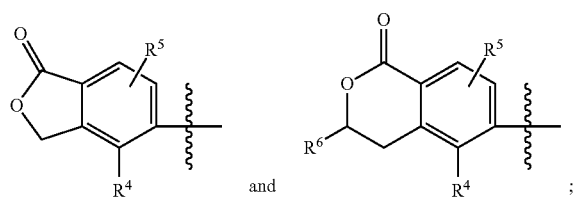

$R^4$ and $R^5$ are each independently selected from the group consisting of hydrogen, alkyl, halogen, cyano, nitro, alkoxy, cycloalkyl, heterocyclyl, aryl and heteroaryl;
$R^6$ is selected from hydrogen, alkyl and halogen;
n is 0, 1 or 2.

In a preferred embodiment of the present invention, a compound of formula (I), or a tautomer, mesomer, racemate, enantiomer, diastereomer, or mixture thereof, or pharmaceutically acceptable salt thereof, wherein $R^1$ is alkyl, wherein the alkyl is optionally further substituted by one or more groups selected from the group consisting of halogen, hydroxyl and alkoxy; $R^1$ is preferably $C_{1-6}$ alkyl, more preferably selected from the group consisting of methyl, ethyl and propyl.

In a preferred embodiment of the present invention, a compound of formula (I), or a tautomer, mesomer, racemate, enantiomer, diastereomer, or mixture thereof, or pharmaceutically acceptable salt thereof, wherein $R^4$ is alkyl, and $R^5$ is hydrogen.

In another preferred embodiment of the present invention, a compound of formula (I), or a tautomer, mesomer, racemate, enantiomer, diastereomer, or mixture thereof, or pharmaceutically acceptable salt thereof, which is a compound of formula (II):

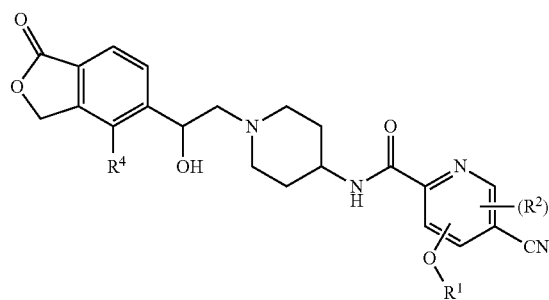

(II)

or a tautomer, mesomer, racemate, enantiomer, diastereomer, or mixture thereof, or pharmaceutically acceptable salt thereof, wherein $R^1$, $R^2$, $R^4$ and n are as defined in formula (I).

In another preferred embodiment of the present invention, a compound of formula (I), or a tautomer, mesomer, racemate, enantiomer, diastereomer, or mixture thereof, or pharmaceutically acceptable salt thereof, which is a compound of formula (III):

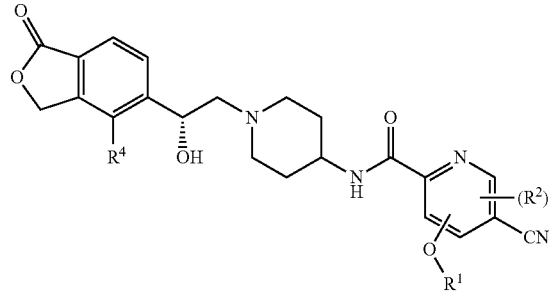

(III)

or a tautomer, mesomer, racemate, enantiomer, diastereomer, or mixture thereof, or pharmaceutically acceptable salt thereof, wherein $R^1$, $R^2$, $R^4$ and n are as defined in formula (I).

In another preferred embodiment of the present invention, a compound of formula (I), or a tautomer, mesomer, racemate, enantiomer, diastereomer, or mixture thereof, or pharmaceutically acceptable salt thereof, which is a compound of formula (IV):

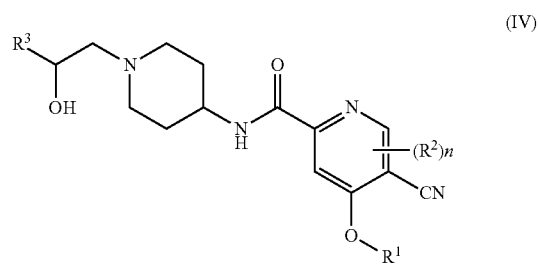

(IV)

or a tautomer, mesomer, racemate, enantiomer, diastereomer, or mixture thereof, or pharmaceutically acceptable salt thereof, wherein $R^1$, $R^2$, $R^3$ and n are as defined in formula (I).

In another preferred embodiment of the present invention, a compound of formula (I), or a tautomer, mesomer, racemate, enantiomer, diastereomer, or mixture thereof, or pharmaceutically acceptable salt thereof, which is a compound of formula (V):

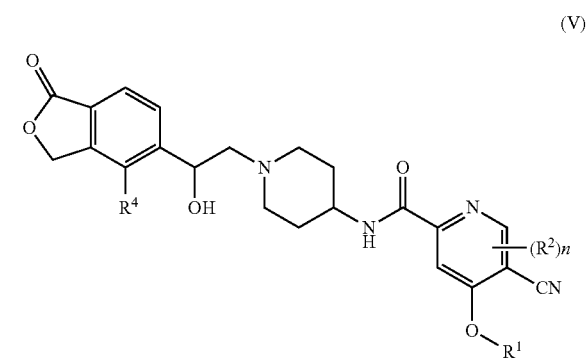

(V)

or a tautomer, mesomer, racemate, enantiomer, diastereomer, or mixture thereof, or pharmaceutically acceptable salt thereof, wherein $R^1$, $R^2$, $R^4$ and n are as defined in formula (I).

In another preferred embodiment of the present invention, a compound of formula (I), or a tautomer, mesomer, racemate, enantiomer, diastereomer, or mixture thereof, or pharmaceutically acceptable salt thereof, which is a compound of formula (VI):

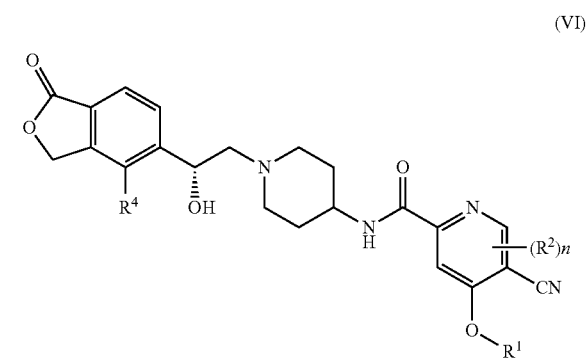

(VI)

or a tautomer, mesomer, racemate, enantiomer, diastereomer, or mixture thereof, or pharmaceutically acceptable salt thereof, wherein $R^1$, $R^2$, $R^4$ and n are as defined in formula (I).

Typical compounds of the present invention include, but are not limited to,

| Example No. | Structure and name |
|---|---|
| 1 | 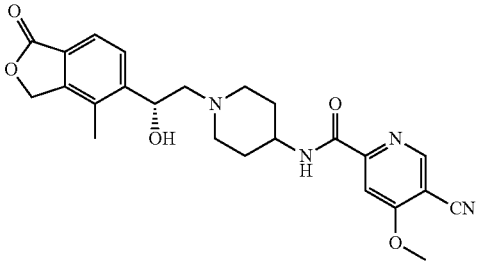

(R)-5-cyano-N-(1-(2-hydroxy-2-(4-methyl-1-oxo-1,3-dihydroisobenzofuran-5-yl)ethyl)piperidin-4-yl)-4-methoxypicolinamide |
| 2 | 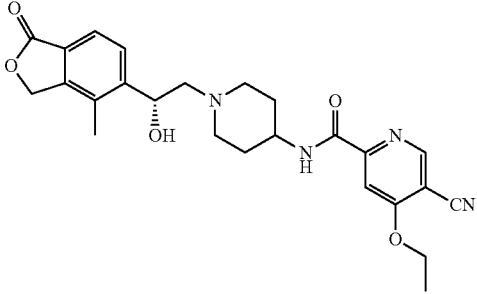 [SMILES: COc1cc(C(=O)NC2CCN(C[C@H](O)c3ccc4c(c3C)COC4=O)CC2)ncc1C#N]

(R)-5-cyano-4-ethoxy-N-(1-(2-hydroxy-2-(4-methyl-1-oxo-1,3-dihydroisobenzofuran-5-yl)ethyl)piperidin-4-yl)picolinamide |
| 3 | 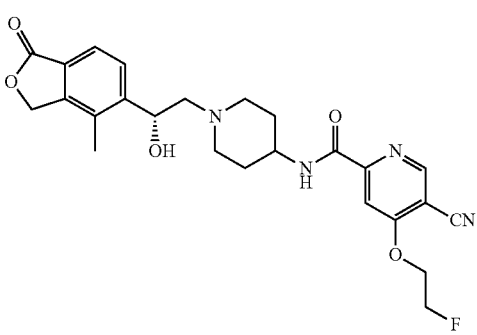

(R)-5-cyano-4-(2-fluoroethoxy)-N-(1-(2-hydroxy-2-(4-methyl-1-oxo-1,3-dihydroisobenzofuran-5-yl)ethyl)piperidin-4-yl)picolinamide |
| 4 | 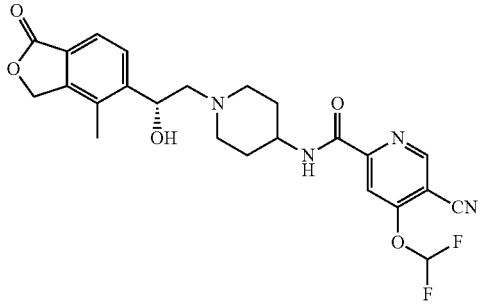

(R)-5-cyano-4-(difluoromethoxy)-N-(1-(2-hydroxy-2-(4-methyl-1-oxo-1,3-dihydroisobenzofuran-5-yl)ethyl)piperidin-4-yl)picolinamide | or a tautomer, mesomer, racemate, enantiomer, diastereomer, or mixture thereof, or pharmaceutically acceptable salt thereof.

The present invention further provides a compound of formula (IA), or a tautomer, mesomer, racemate, enantiomer, diastereomer, or mixture thereof, or pharmaceutically acceptable salt thereof, as the intermediate for the preparation of the compound of formula (I):

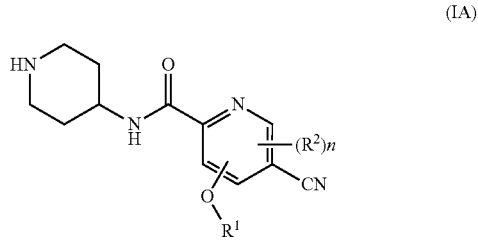

(IA)

wherein $R^1$ is alkyl, wherein the alkyl is optionally further substituted by one or more groups selected from the group consisting of halogen, hydroxyl, alkoxy, cycloalkyl, heterocyclyl, aryl, heteroaryl, carboxyl and carboxylic ester;

$R^2$ is selected from the group consisting of hydrogen, alkyl, halogen, cyano, nitro, alkoxy, cycloalkyl and heterocyclyl, wherein the alkyl, alkoxy, cycloalkyl or heterocyclyl is optionally further substituted by one or more groups selected from the group consisting of alkyl, halogen hydroxyl, hydroxyalkyl, alkoxy, cycloalkyl, heterocyclyl, aryl, heteroaryl, carboxyl and carboxylic ester;

which can be used as the intermediate in the preparation of the compound of formula (I), or a tautomer, mesomer, racemate, enantiomer, diastereomer, or mixture thereof, or pharmaceutically acceptable salt thereof;

n is 0, 1 or 2.

In another preferred embodiment of the present invention, a compound of formula (IA), or a tautomer, mesomer, racemate, enantiomer, diastereomer, or mixture thereof, or pharmaceutically acceptable salt thereof, which is a compound of formula (IVA):

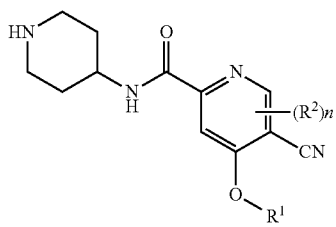

or a tautomer, mesomer, racemate, enantiomer, diastereomer, or mixture thereof, or pharmaceutically acceptable salt thereof; which can be used as the intermediate in the preparation of the compound of formula (IV), or a tautomer, mesomer, racemate, enantiomer, diastereomer, or mixture thereof, or pharmaceutically acceptable salt thereof; wherein $R^1$, $R^2$ and n are as defined in formula (IA).

Typical compounds of formula (IA) include, but are not limited to:

| Example No. | Structure and name |
| --- | --- |
| 1e | |

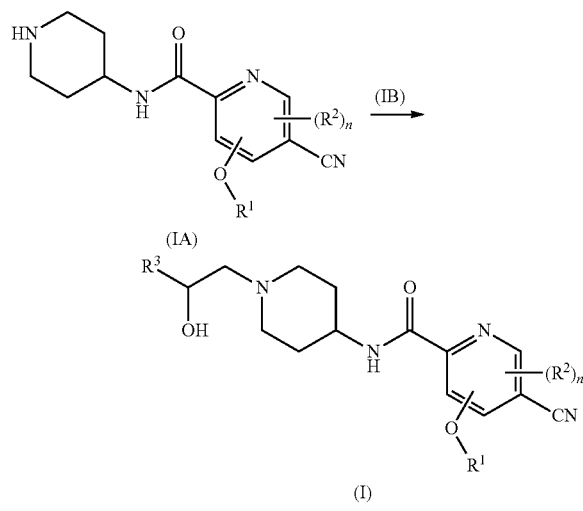

1e 5-cyano-4-methoxy-N-(piperidin-4-yl)picolinamide or a tautomer, mesomer, racemate, enantiomer, diastereomer, or mixture thereof, or pharmaceutically acceptable salt thereof.

In another aspect, the present invention provides a process for preparing the compound of formula (I), or a tautomer, mesomer, racemate, enantiomer, diastereomer, or mixture thereof, or pharmaceutically acceptable salt thereof, comprising a step of:

heating a compound of formula (IA) with a substituted benzofuran derivative of formula (IB), preferably with (R)-4-methyl-5-(oxiran-2-yl)isobenzofuran-1(3H)-one, to give a compound of formula (I);

wherein $R^1$ to $R^3$ and n are as defined in general formula (I).

Another aspect of this invention is directed to a pharmaceutical composition comprising a therapeutically effective amount of the compound of formula (I), or a tautomer, mesomer, racemate, enantiomer, diastereomer, or mixture thereof, or pharmaceutically acceptable salt thereof, and pharmaceutically acceptable carriers, diluents or excipients.

Another aspect of this invention is directed to use of a compound of formula (I), or a tautomer, mesomer, racemate, enantiomer, diastereomer, or mixture thereof, or pharmaceutically acceptable salt thereof, or pharmaceutical composition comprising the same, in the preparation of a ROMK inhibitor.

Another aspect of this invention is directed to use of a compound of formula (I), or a tautomer, mesomer, racemate, enantiomer, diastereomer, or mixture thereof, or pharmaceutically acceptable salt thereof, or pharmaceutical composition comprising the same, in the preparation of a medicament for the treatment or prevention of hypertension and/or heart failure.

Another aspect of this invention is directed to use of a compound of formula (I), or a tautomer, mesomer, racemate, enantiomer, diastereomer, or mixture thereof, or pharmaceutically acceptable salt thereof, or pharmaceutical composition comprising the same, in the preparation of a medicament for the treatment or prevention of ROMK mediated diseases, wherein said diseases are preferably selected from the group consisting of hepatic cirrhosis, acute and chronic renal insufficiency, nephrotic syndrome, pulmonary hypertension, cardiovascular disease, myocardial infarction, stroke, cardiac insufficiency, pulmonary hypertonia, atherosclerosis and kidney stones.

Another aspect of this invention is directed to a compound of formula (I), or a tautomer, mesomer, racemate, enantiomer, diastereomer, or mixture thereof, or pharmaceutically acceptable salt thereof, or pharmaceutical composition comprising the same, for use as a ROMK inhibitor.

Another aspect of this invention is directed to a compound of formula (I), or a tautomer, mesomer, racemate, enantiomer, diastereomer, or mixture thereof, or pharmaceutically acceptable salt thereof, or pharmaceutical composition comprising the same, for use in the treatment or prevention of hypertension and/or heart failure.

Another aspect of this invention is directed to a compound of formula (I), or a tautomer, mesomer, racemate, enantiomer, diastereomer, or mixture thereof, or pharmaceutically acceptable salt thereof, or pharmaceutical composition comprising the same, for use in the treatment or prevention of ROMK mediated diseases, wherein said diseases are preferably selected from the group consisting of hepatic cirrhosis, acute and chronic renal insufficiency, nephrotic syndrome, pulmonary hypertension, cardiovascular disease, myocardial infarction, stroke, cardiac insufficiency, pulmonary hypertonia, atherosclerosis and kidney stones.

Another aspect of this invention is directed to a method for inhibiting ROMK, comprising administering to a patient in need thereof a therapeutically effective amount of a compound of formula (I), or a tautomer, mesomer, racemate, enantiomer, diastereomer, or mixture thereof, or pharmaceutically acceptable salt thereof, or the pharmaceutical composition comprising the same.

Another aspect of this invention is directed to a method for the treatment or prevention of hypertension and/or heart failure, comprising administering to a patient in need thereof a therapeutically effective amount of the compound of formula (I), or a tautomer, mesomer, racemate, enantiomer, diastereomer, or mixture thereof, or pharmaceutically acceptable salt thereof, or a pharmaceutical composition comprising the same.

Another aspect of this invention is directed to a method for the treatment or prevention of a ROMK-mediated disease or disorder, comprising administering to a patient in need thereof a therapeutically effective amount of a compound of formula (I), or a tautomer, mesomer, racemate, enantiomer, diastereomer, or mixture thereof, or pharmaceutically acceptable salt thereof, or a pharmaceutical composition comprising the same, wherein the disease or disorder is preferably selected from the group consisting of hepatic cirrhosis, acute and chronic renal insufficiency, nephrotic syndrome, pulmonary hypertension, cardiovascular disease, myocardial infarction, stroke, cardiac insufficiency, pulmonary hypertonia, atherosclerosis and kidney stones.

The pharmaceutical compositions containing the active ingredient can be in a form suitable for oral administration, such as a tablet, troche, lozenge, aqueous or oily suspension, dispersible powder or granule, emulsion, hard or soft capsule, or syrup or elixir. Oral compositions can be prepared according to any known method for the preparation of pharmaceutical compositions in the art. Such compositions can contain one or more additives selected from the group consisting of sweeteners, flavoring agents, colorants and preservatives, in order to provide a pleasing and palatable pharmaceutical formulation. A tablet contains the active ingredient and nontoxic pharmaceutically acceptable excipients suitable for the manufacture of the tablet. These excipients can be inert excipients, such as calcium carbonate, sodium carbonate, lactose, calcium phosphate or sodium phosphate; granulating and disintegrating agents, such as microcrystalline cellulose, cross-linked sodium carboxymethyl cellulose, corn starch or alginic acid; binders, such as starch, gelatin, polyvinylpyrrolidone or acacia; and lubricants, such as magnesium stearate, stearic acid or talc. The tablet can be uncoated or coated by means of known techniques, which can mask drug taste or delay the disintegration and absorption of the active ingredient in the gastrointestinal tract, thereby providing sustained release over an extended period. For example, a water soluble taste masking material can be used, such as hydroxypropyl methylcellulose or hydroxypropyl cellulose, or an extended release material can be used, such as ethyl cellulose, or cellulose acetate butyrate.

Oral formulations can also be provided as hard gelatin capsules in which the active ingredient is mixed with an inert solid diluent, such as calcium carbonate, calcium phosphate or kaolin, or as soft gelatin capsules in which the active ingredient is mixed with a water soluble carrier, such as polyethylene glycol or an oil medium, for example peanut oil, liquid paraffin, or olive oil.

Aqueous suspensions contain the active ingredient in admixture with excipients suitable for the manufacture of aqueous suspensions. Such excipients are suspending agents, such as sodium carboxymethylcellulose, methylcellulose, hydroxypropylmethylcellulose, sodium alginate, polyvinylpyrrolidone and gum acacia; dispersants or humectants, which can be a naturally occurring phosphatide, such as lecithin, or a condensation product of an alkylene oxide with fatty acid, such as polyoxyethylene stearate, or a condensation product of ethylene oxide with a long chain aliphatic alcohol, such as heptadecaethyleneoxy cetanol, or condensation products of ethylene oxide with part esters derived from fatty acids and hexitols, such as polyoxyethylene sorbitol monooleate, or condensation products of ethylene oxide with partial esters derived from fatty acids and hexitol anhydrides, such as polyoxyethylene sorbitan monooleate. The aqueous suspensions can also contain one or more preservatives, such as ethylparaben or n-propylparaben, one or more colorants, one or more flavoring agents, and one or more sweeteners, such as sucrose, saccharin or aspartame.

Oil suspensions can be formulated by suspending the active ingredient in a vegetable oil, such as arachis oil, olive oil, sesame oil or coconut oil, or in a mineral oil, such as liquid paraffin. The oil suspension can contain a thickener, such as beeswax, hard paraffin or cetyl alcohol. The aforesaid sweetener and flavoring agent can be added to provide a palatable preparation. These compositions can be preserved by adding an antioxidant, such as butylated hydroxyanisole or α-tocopherol.

The active ingredient and the dispersant or wetting agent, suspending agent or one or more preservatives can be provided by adding water to prepare dispersible powder and granules suitable for the preparation of an aqueous suspension. Suitable dispersants or wetting agents and suspending agents are exemplified by those already mentioned above. Additional excipients, such as a sweetener, flavoring agent and colorant, can also be added. These compositions can be preserved by adding an antioxidant such as ascorbic acid.

The present pharmaceutical composition can also be in the form of an oil-in-water emulsion. The oil phase can be a vegetable oil, such as olive oil or arachis oil, or a mineral oil, such as liquid paraffin or a mixture thereof. Suitable emulsifying agents can be naturally occurring phosphatides, such as soy bean lecithin, and esters or partial esters derived from fatty acids and hexitol anhydrides, such as sorbitan monooleate, and condensation products of the aforementioned partial esters with ethylene oxide, such as polyoxyethylene sorbitol monooleate. The emulsion can also contain a sweetener, flavoring agent, preservative and antioxidant. Syrups and elixirs can be formulated with a sweetener, such as glycerol, propylene glycol, sorbitol or sucrose. Such formulations can also contain a demulcent, a preservative, a colorant and an antioxidant.

The pharmaceutical composition can be in the form of a sterile injectable aqueous solution. The acceptable vehicles and solvents that can be employed are water, Ringer's solution and isotonic sodium chloride solution. The sterile injectable preparation can also be a sterile injectable oil-in-water microemulsion in which the active ingredient is dissolved in the oil phase. For example, the active ingredient can be firstly dissolved in a mixture of soybean oil and lecithin, the oil solution is then introduced into a mixture of water and glycerol and processed to form a microemulsion. The injectable solution or microemulsion can be introduced into an individual's bloodstream by local bolus injection. Alternatively, it may be advantageous to administer the solution or microemulsion in such a way as to maintain a constant circulating concentration of the present compound. In order to maintain such a constant concentration, a continuous intravenous delivery device can be utilized. An example of such device is Deltec CADD-PLUS™ 5400 intravenous injection pump.

The pharmaceutical composition can be in the form of a sterile injectable aqueous or oily suspension for intramuscular and subcutaneous administration. Such a suspension can be formulated with suitable dispersants or wetting agents and suspending agents as described above according to known techniques. The sterile injectable preparation can also be a sterile injectable solution or suspension prepared in a nontoxic parenterally acceptable diluent or solvent, for example, a solution prepared in 1,3-butanediol. Moreover, sterile fixed oils can easily be used as a solvent or suspending medium. For this purpose, any blending fixed oils including synthetic mono- or di-glyceride can be employed. Moreover, fatty acids, such as oleic acid, can be employed in the preparation of an injectable.

The present compound can be administered in the form of a suppository for rectal administration. These pharmaceutical compositions can be prepared by mixing drug with a suitable non-irritating excipient that is solid at ordinary temperatures, but liquid in the rectum, thereby melting in the rectum to release the drug. Such materials include cocoa butter, glycerin, gelatin, hydrogenated vegetable oils, mixtures of polyethylene glycols and fatty acid esters of polyethylene glycol with various molecular weights.

It is well known to those skilled in the art that the dosage of a drug depends on a variety of factors including, but not limited to, the following factors: activity of the specific compound, age, weight, general health, behavior, and diet of the patient, administration time, administration route, excretion rate, drug combination and the like. In addition, the best treatment, such as treatment mode, daily dose of the compound of formula (I) or the type of pharmaceutically acceptable salt thereof can be verified by the traditional therapeutic regimen.

Definitions

Unless otherwise stated, the terms used herein have the following meanings.

"Alkyl" refers to a linear or branched saturated aliphatic hydrocarbon group having 1 to 20 carbon atoms, preferably $C_1$ to $C_{10}$ alkyl, more preferably $C_1$ to $C_6$ alkyl. Nonlimiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and the branched isomers thereof. More preferably, an alkyl group is a lower alkyl having 1 to 6 carbon atoms, and nonlimiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. The alkyl group can be substituted or unsubstituted. When substituted, the substituent group(s) can be substituted at any available connection point. The substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocyclic alkoxy, cycloalkylthio, heterocyclylthio, oxo, amino, haloalkyl, hydroxyalkyl, carboxyl, carboxylic ester.

"Cycloalkyl" refers to a saturated and/or partially unsaturated monocyclic or polycyclic hydrocarbon group having 3 to 20 carbon atoms, preferably 3 to 12 carbon atoms, more preferably 3 to 10 carbon atoms, and most preferably 3 to 6 carbon atoms. Nonlimiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like, preferably cyclopropyl and cyclohexenyl. Polycyclic cycloalkyl includes a cycloalkyl having a spiro ring, fused ring or bridged ring.

"Spiro cycloalkyl" refers to a 5 to 20-membered polycyclic group with rings connected through one common carbon atom (called a spiro atom), wherein one or more rings can contain one or more double bonds, but none of the rings has a completely conjugated pi-electron system, preferably 6 to 14-membered spiro cycloalkyl, and more preferably 7 to 10-membered spiro cycloalkyl. According to the number of common spiro atoms, spiro cycloalkyl can be divided into mono-spiro cycloalkyl, di-spiro cycloalkyl, or poly-spiro cycloalkyl, and preferably a mono-spiro cycloalkyl or di-spiro cycloalkyl, more preferably 4-membered/4-membered, 4-membered/5-membered, 4-membered/6-membered, 5-membered/5-membered, or 5-membered/6-membered mono-spiro cycloalkyl. Unlimited examples of spiro cycloalkyls include, but are not limited to:

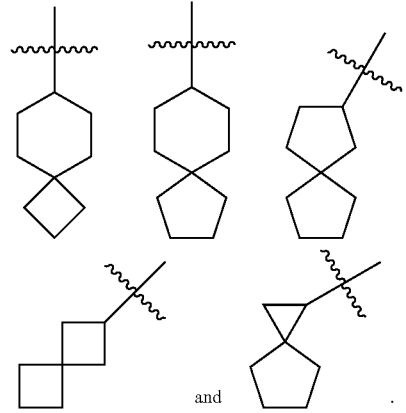

and

"Fused cycloalkyl" refers to a 5 to 20-membered full-carbon polycyclic group, wherein each ring in the system shares an adjacent pair of carbon atoms with another ring, wherein one or more rings can contain one or more double bonds, but none of the rings has a completely conjugated pi-electron system, preferably 6 to 14 membered fused cycloalkyl, more preferably 7 to 10 membered fused cycloalkyl. According to the number of membered rings, fused cycloalkyl can be divided into bicyclic, tricyclic, tetracyclic or polycyclic fused cycloalkyl, preferably bicyclic or tricyclic fused cycloalkyl, and more preferably 5-membered/5-membered, or 5-membered/6-membered bicyclic fused cycloalkyl. Nonlimiting examples of fused cycloalkyl include, but are not limited to:

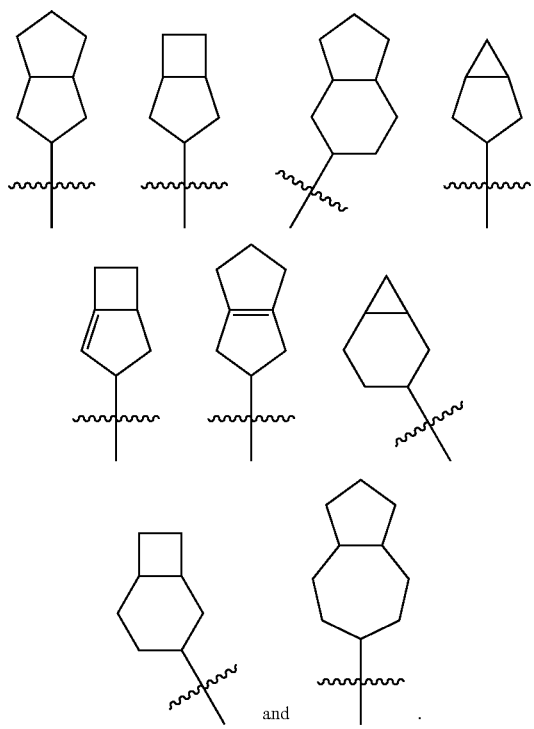

"Bridged cycloalkyl" refers to a 5 to 20-membered full-carbon polycyclic group, wherein every two rings in the system share two disconnected atoms, wherein the rings can have one or more double bonds, but none of the rings has a completely conjugated pi-electron system, preferably 6 to 14-membered bridged cycloalkyl, and more preferably 7 to 10-membered bridged cycloalkyl. According to the number of membered rings, bridged cycloalkyl can be divided into bicyclic, tricyclic, tetracyclic or polycyclic bridged cycloalkyl, and preferably bicyclic, tricyclic or tetracyclic bridged cycloalkyl, and more preferably bicyclic or tricyclic bridged cycloalkyl. Nonlimiting examples of bridged cycloalkyls include, but are not limited to:

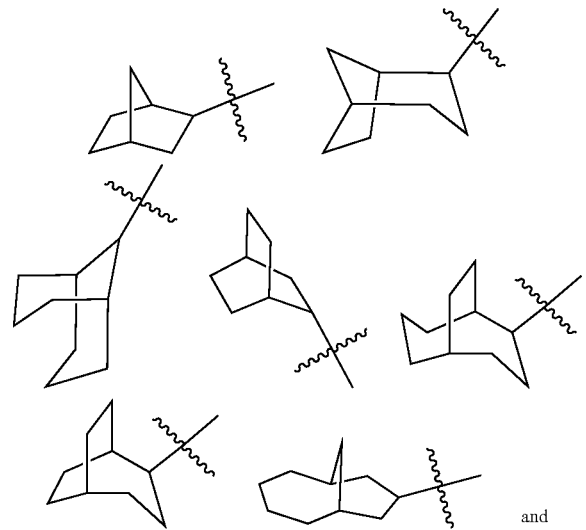

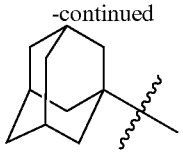

Said cycloalkyl can be fused to aryl, heteroaryl or heterocyclyl, wherein the ring bound to the parent structure is cycloalkyl. Nonlimiting examples include indanyl, tetrahydronaphthyl, benzocycloheptyl and the like. The cycloalkyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclylthio, oxo, amino, haloalkyl, hydroxyalkyl, carboxyl, and carboxylic ester.

"Heterocyclyl" refers to a 3 to 20-membered saturated and/or partially unsaturated monocyclic or polycyclic hydrocarbon group having one or more heteroatoms selected from the group consisting of N, O, and $S(O)_m$ (wherein m is an integer selected from 0 to 2) as ring atoms, but excluding —O—O—, —O—S— or —S—S— in the ring, and the remaining ring atoms being carbon atoms. Preferably, heterocyclyl has 3 to 12 atoms with 1 to 4 heteroatoms, more preferably 3 to 10 atoms with 1 to 3 heteroatoms, and most preferably 5 to 6 atoms with 1 to 2 heteroatoms. Nonlimiting examples of monocyclic heterocyclyl include, but are not limited to, pyrrolidinyl, piperidyl, piperazinyl, morpholinyl, thiomorpholinyl, homopiperazinyl, pyranyl, tetrahydrofuranyl, and the like. Polycyclic heterocyclyl includes a heterocyclyl having a spiro ring, fused ring or bridged ring.

"Spiro heterocyclyl" refers to a 5 to 20-membered polycyclic heterocyclyl with rings connected through one common atom (called a spiro atom), wherein said rings have one or more heteroatoms selected from the group consisting of N, O, and $S(O)_m$ (wherein m is an integer selected from 0 to 2) as ring atoms and the remaining ring atoms being carbon atoms, wherein one or more rings can contain one or more double bonds, but none of the rings has a completely conjugated pi-electron system; preferably 6 to 14-membered spiro heterocyclyl, and more preferably 7 to 10-membered spiro heterocyclyl. According to the number of common spiro atoms, spiro heterocyclyl can be divided into mono-spiro heterocyclyl, di-spiro heterocyclyl, or poly-spiro heterocyclyl, preferably mono-spiro heterocyclyl or di-spiro heterocyclyl, and more preferably 4-membered/4-membered, 4-membered/5-membered, 4-membered/6-membered, 5-membered/5-membered, or 5-membered/6-membered mono-spiro heterocyclyl. Nonlimiting examples of spiro heterocyclyls include, but are not limited to:

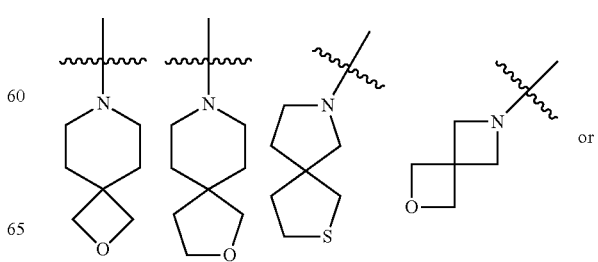

-continued

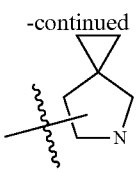

"Fused heterocyclyl" refers to a 5 to 20-membered polycyclic heterocyclyl group, wherein each ring in the system shares an adjacent pair of atoms with another ring, wherein one or more rings can contain one or more double bonds, but none of the rings has a completely conjugated pi-electron system, and wherein said rings have one or more heteroatoms selected from the group consisting of N, O, and $S(O)_m$ (wherein m is an integer selected from 0 to 2) as ring atoms, and the remaining ring atoms being carbon atoms; preferably 6 to 14-membered fused heterocyclyl, and more preferably 7 to 10-membered fused heterocyclyl. According to the number of membered rings, fused heterocyclyl can be divided into bicyclic, tricyclic, tetracyclic or polycyclic fused heterocyclyl, preferably bicyclic or tricyclic fused heterocyclyl, and more preferably 5-membered/5-membered, or 5-membered/6-membered bicyclic fused heterocyclyl. Nonlimiting examples of fused heterocyclyl include, but are not limited to:

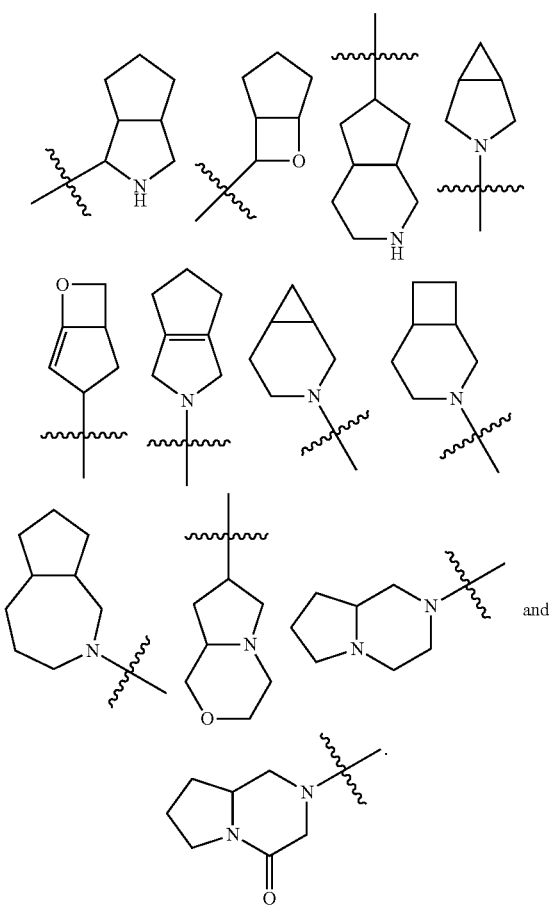

"Bridged heterocyclyl" refers to a 5 to 14-membered polycyclic heterocyclyl group, wherein every two rings in the system share two disconnected atoms, wherein the rings can have one or more double bonds, but none of the rings has a completely conjugated pi-electron system, and the rings have one or more heteroatoms selected from the group consisting of N, O, and $S(O)_m$ (wherein m is an integer selected from 0 to 2) as ring atoms, and the remaining ring atoms being carbon atoms; preferably 6 to 14-membered bridged heterocyclyl, and more preferably 7 to 10-membered bridged heterocyclyl. According to the number of membered rings, bridged heterocyclyl can be divided into bicyclic, tricyclic, tetracyclic or polycyclic bridged heterocyclyl, and preferably bicyclic, tricyclic or tetracyclic bridged heterocyclyl, and more preferably bicyclic or tricyclic bridged heterocyclyl. Nonlimiting examples of bridged heterocyclyls include, but are not limited to:

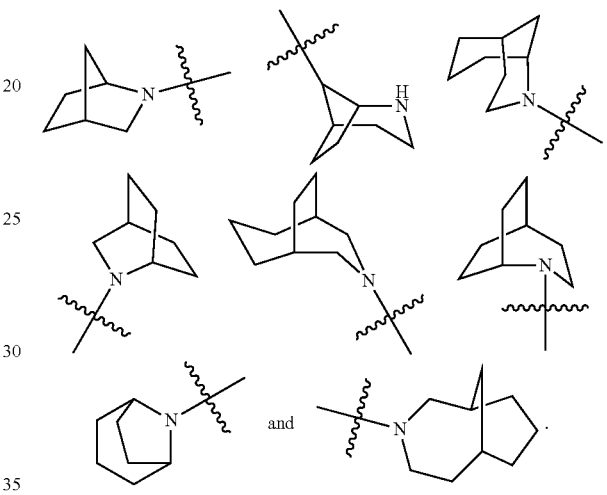

Said heterocyclyl can be fused to aryl, heteroaryl or cycloalkyl, wherein the ring bound to the parent structure is heterocyclyl. Nonlimiting examples include, but are not limited to:

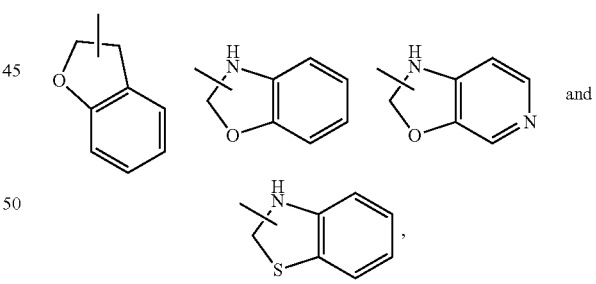

etc.

The heterocyclyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocylylthio, oxo, amino, haloalkyl, hydroxyalkyl, carboxyl, and carboxylic ester.

"Aryl" refers to a 6 to 14-membered full-carbon monocyclic ring or polycyclic fused ring (i.e. each ring in the system shares an adjacent pair of carbon atoms with another ring in the system) having a completely conjugated pi-electron system; preferably 6 to 10-membered aryl, more preferably phenyl and naphthyl, and most preferably phenyl. The aryl can be fused to heteroaryl, heterocyclyl or cycloalkyl, wherein the ring bound to the parent structure is aryl. Nonlimiting examples include, but are not limited to:

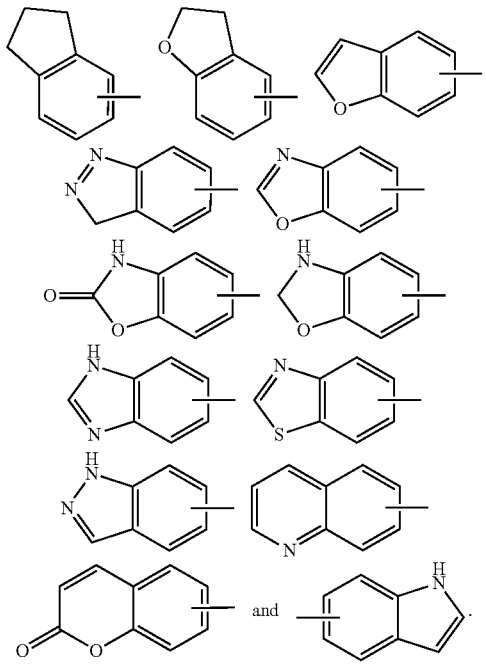

The aryl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclylthio, amino, haloalkyl, hydroxyalkyl, carboxyl, and carboxylic ester.

"Heteroaryl" refers to a 5 to 14-membered aryl having 1 to 4 heteroatoms selected from the group consisting of O, S and N as ring atoms and the remaining ring atoms being carbon atoms; preferably 5 to 10-membered heteroaryl, more preferably 5- or 6-membered heteroaryl, such as furyl, thienyl, pyridyl, pyrrolyl, N-alkyl pyrrolyl, pyrimidinyl, pyrazinyl, imidazolyl, tetrazolyl and the like. The heteroaryl can be fused to aryl, heterocyclyl or cycloalkyl, wherein the ring bound to the parent structure is heteroaryl. Nonlimiting examples include, but are not limited to:

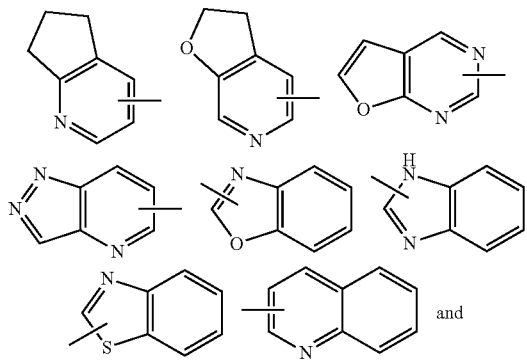

-continued

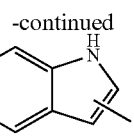

The heteroaryl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclylthio, amino, haloalkyl, hydroxyalkyl, carboxyl, and carboxylic ester.

"Alkoxy" refers to an —O-(alkyl) or an —O-(unsubstituted cycloalkyl) group, wherein the alkyl is as defined above. Nonlimiting examples include, but are not limited to, methoxy, ethoxy, propoxy, butoxy, cyclopropyloxy, cyclobutyloxy, cyclopentyloxy, cyclohexyloxy, and the like. The alkoxy can be optionally substituted or unsubstituted. When substituted, the substituent is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclylthio, amino, haloalkyl, hydroxyalkyl, carboxyl, and carboxylic ester.

"Haloalkyl" refers to an alkyl substituted with one or more halogens, wherein alkyl is as defined above.

"Hydroxy" refers to an —OH group.

"Hydroxyalkyl" refers to an alkyl substituted with hydroxy, wherein alkyl is as defined above.

"Halogen" refers to fluorine, chlorine, bromine or iodine.

"Cyano" refers to a —CN group.

"Carboxyl" refers to a —C(O)OH group.

"Carboxylic ester" refers to a —C(O)O(alkyl) or (cycloalkyl) group, wherein the alkyl and cycloalkyl are as defined above.

"Optional" or "optionally" means that the event or circumstance described subsequently can, but need not, occur, and such description includes the situation in which the event or circumstance may or may not occur. For example, "the heterocyclic group optionally substituted with an alkyl" means that an alkyl group can be, but need not be, present, and such description includes the situation of the heterocyclic group being substituted with an alkyl and the heterocyclic group being not substituted with an alkyl.

"Substituted" refers to one or more hydrogen atoms in a group, preferably up to 5, more preferably 1 to 3 hydrogen atoms, independently substituted with a corresponding number of substituents. It goes without saying that the substituents only exist in their possible chemical position. The person skilled in the art is able to determine whether the substitution is possible or impossible by experiments or theory without paying excessive efforts. For example, when amino or hydroxy having a free hydrogen is bound to a carbon atom having unsaturated bonds (such as olefinic), it may be unstable.

A "pharmaceutical composition" refers to a mixture of one or more of the compounds according to the present invention or physiologically/pharmaceutically acceptable salts or prodrugs thereof and other chemical components such as physiologically/pharmaceutically acceptable carriers and excipients. The purpose of a pharmaceutical composition is to facilitate administration of a compound to an organism and the absorption of the active ingredient, thus displaying biological activity.

Synthesis Method of the Present Invention

In order to obtain the object of the present invention, the present invention applies the following synthetic technical solutions.

A process for preparing a compound of formula (I) of the present invention, or a tautomer, mesomer, racemate, enantiomer, diastereomer, or mixture thereof, or pharmaceutically acceptable salt thereof, comprising the following steps:

Scheme 1

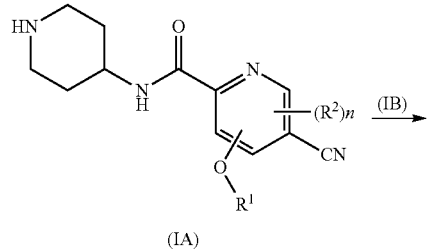

(IA)

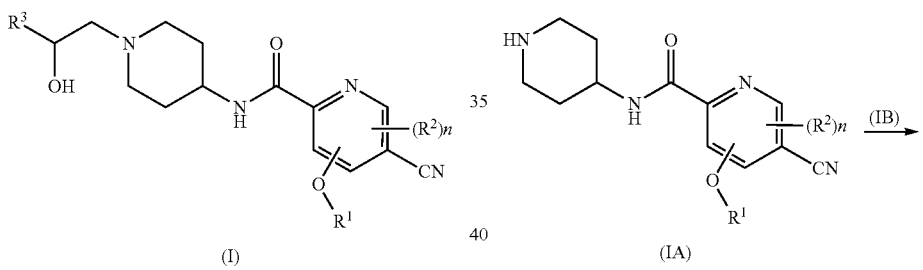

heating a compound of formula (IA) with a compound of substituted benzofuran derivatives (IB), preferably (R)-4-methyl-5-(oxiran-2-yl)isobenzofuran-1(3H)-one in an organic solvent to give a compound of formula (I), wherein $R^1$ to $R^3$ and n are as defined in general formula (I).

A process for preparing a compound of formula (II), or a tautomer, mesomer, racemate, enantiomer, diastereomer, or mixture thereof, or pharmaceutically acceptable salt thereof, comprising the following steps:

Scheme 2

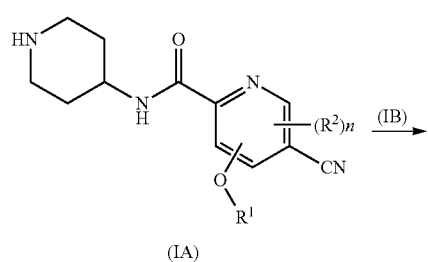

(IA)

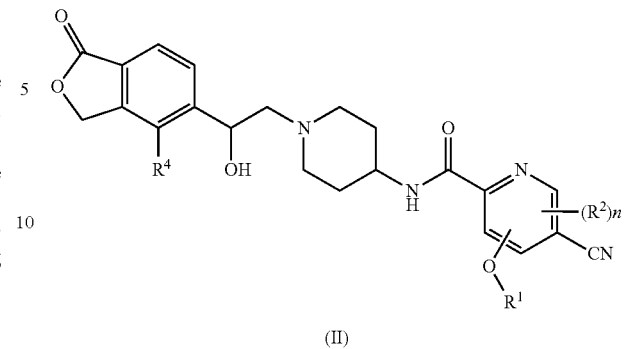

(II)

heating a compound of formula (IA) with a compound of substituted benzofuran derivatives (IB), preferably (R)-4-methyl-5-(oxiran-2-yl)isobenzofuran-1(3H)-one in an organic solvent to give a compound of formula (II), wherein $R^1$, $R^2$, $R^4$ and n are as defined in general formula (II).

A process for preparing a compound of formula (III), or a tautomer, mesomer, racemate, enantiomer, diastereomer, or mixture thereof, or pharmaceutically acceptable salt thereof, comprising the following steps:

Scheme 3

(IA)

(III)

heating a compound of formula (IA) with a compound of substituted benzofuran derivatives (TB), preferably (R)-4-methyl-5-(oxiran-2-yl)isobenzofuran-1(3H)-one in an organic solvent to give a compound of formula (III), wherein $R^1$, $R^2$, $R^4$ and n are as defined in general formula (III).

A process for preparing a compound of formula (IV), or a tautomer, mesomer, racemate, enantiomer, diastereomer, or mixture thereof, or pharmaceutically acceptable salt thereof, comprising the following steps:

Scheme 4

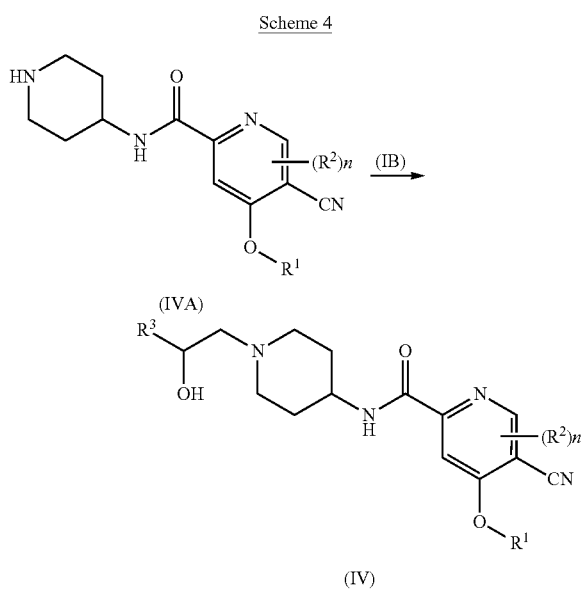

heating a compound of formula (IVA) with a compound of substituted benzofuran derivatives (IB), preferably (R)-4-methyl-5-(oxiran-2-yl)isobenzofuran-1(3H)-one in an organic solvent to give a compound of formula (IV), wherein $R^1$ to $R^3$ and n are as defined in general formula (I).

A process for preparing a compound of formula (V), or a tautomer, mesomer, racemate, enantiomer, diastereomer, or mixture thereof, or pharmaceutically acceptable salt thereof, comprising the following steps:

Scheme 5

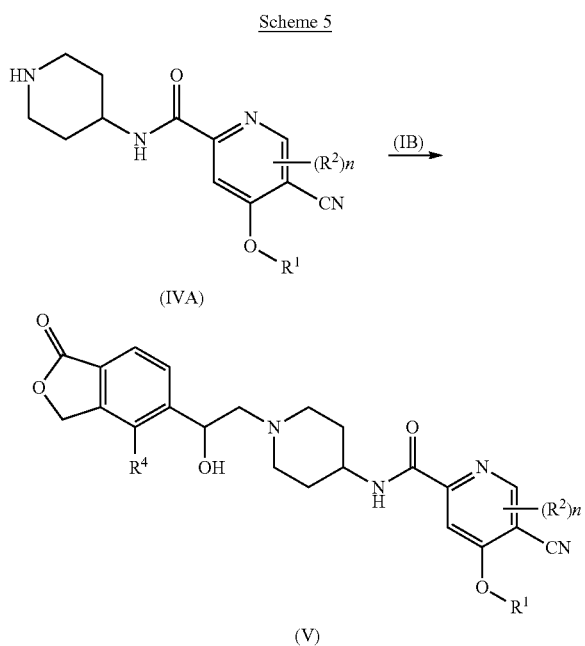

heating a compound of formula (IVA) with a compound of substituted benzofuran derivatives (IB), preferably (R)-4-methyl-5-(oxiran-2-yl)isobenzofuran-1(3H)-one in an organic solvent to give a compound of formula (V), wherein $R^1$, $R^2$, $R^4$ and n are as defined in general formula (I).

A process for preparing a compound of formula (VI), or a tautomer, mesomer, racemate, enantiomer, diastereomer, or mixture thereof, or pharmaceutically acceptable salt thereof, comprising the following steps:

Scheme 6

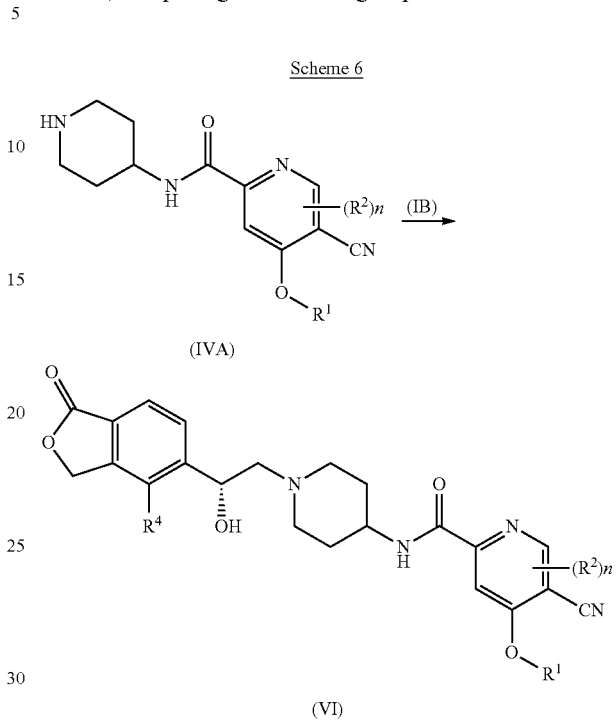

heating a compound of formula (IVA) with a compound of substituted benzofuran derivatives (IB), preferably (R)-4-methyl-5-(oxiran-2-yl)isobenzofuran-1(3H)-one in an organic solvent to give a compound of formula (VI), wherein $R^1$, $R^2$, $R^4$ and n are as defined in general formula (I).

The solvent includes, but is not limited to, acetic acid, methanol, ethanol, acetonitrile, tetrahydrofuran, dichloromethane, dimethyl sulfoxide, 1,4-dioxane, water, N,N-dimethylformamide, or N,N-dimethylacetamide, preferably a nonpolar solvent, more preferably acetonitrile.

DETAILED DESCRIPTION OF THE INVENTION

Figure 1:
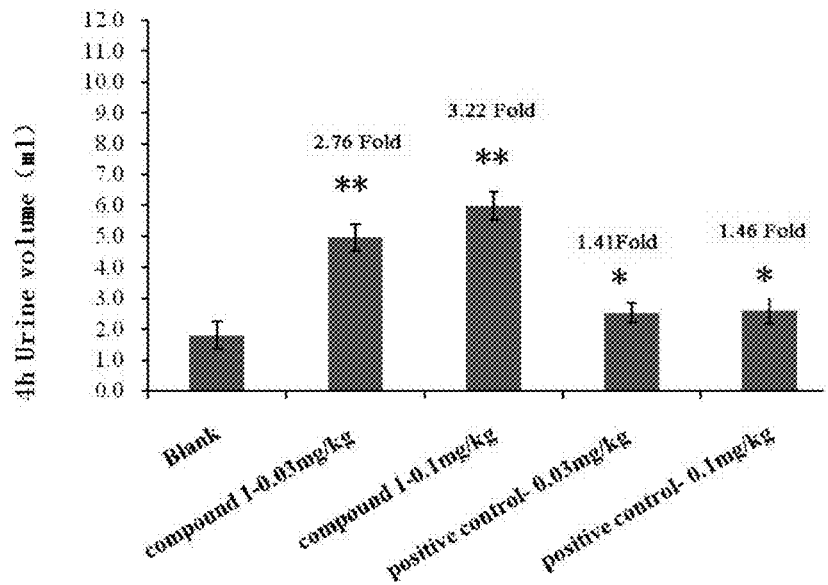
FIG. 1 shows the effect of a ROMK inhibitor on urine volume of SD rats.

The present invention will be further described with the following examples, but the examples should not be considered as limiting the scope of the invention.

Conditions that are not specified in the examples were the common conditions in the art or the recommended conditions of the raw materials by the product manufacturer. For the reagents which are not indicated, the origin was the commercially available conventional reagents.

EXAMPLES

The structure of the compounds were identified by nuclear magnetic resonsance (NMR) and/or mass spectrometry (MS). NMR was determined by Bruker AVANCE-400. The solvents were deuterated-dimethyl sulfoxide (DMSO-$d_6$), deuterated-chloroform (CDCl$_3$) and deuterated-methanol (CD$_3$OD) with tetramethylsilane (TMS) as an internal standard. NMR chemical shifts (δ) are given in $10^{-6}$ (ppm).

MS was determined by a FINNIGAN LCQAd (ESI) mass spectrometer (manufacturer: Thermo, type: Finnigan LCQ advantage MAX).

Yantai Huanghai HSGF254 or Qingdao GF254 silica gel plate was used for thin-layer silica gel chromatography (TLC). The dimension of the silica gel plate used in TLC was 0.15 mm to 0.2 mm, and the dimension of the silica gel plate used in product purification was 0.4 mm to 0.5 mm.

Yantai Huanghai 200 to 300 mesh silica gel was used as carrier for column chromatography.

The known raw materials of the present invention were prepared by the conventional synthesis methods in the art, or can be purchased from ABCR GmbH & Co. KG, Acros Organnics, Aldrich Chemical Company, Accela ChemBio Inc., or Dari chemical Company, etc.

Unless otherwise stated, the reactions were carried out under nitrogen atmosphere or argon atmosphere.

The term "nitrogen atmosphere" or "argon atmosphere" means that a reaction flask was equipped with a 1 L nitrogen or argon balloon.

The term "hydrogen atmosphere" means that a reaction flask was equipped with a 1 L hydrogen balloon.

CEM Discover-S 908860 type microwave reactor was used in microwave reactions.

Unless otherwise stated, the solution used in the reactions refers to an aqueous solution.

Unless otherwise stated, the reaction temperature in the reactions refers to room temperature. Room temperature is the optimum reaction temperature which is in the range of 20° C. to 30° C.

The reaction process was monitored by thin layer chromatography (TLC), and the elution systems included: A: dichloromethane and methanol, B: n-hexane and ethyl acetate, C: petroleum ether and ethyl acetate, D: acetone. The ratio of the volume of the solvent was adjusted according to the polarity of the compounds.

The elution systems for purification of the compounds by column chromatography and thin layer chromatography included: A: dichloromethane and methanol, B: n-hexane and ethyl acetate, C: n-hexane and acetone, D: n-hexane, E: ethyl acetate. The ratio of the volume of the solvent was adjusted according to the polarity of the compounds, and sometimes a little alkaline reagent such as triethylamine or acidic reagent was added.

Example 1

(R)-5-cyano-N-(1-(2-hydroxy-2-(4-methyl-1-oxo-1,3-dihydroisobenzofuran-5-yl)ethyl)piperidin-4-yl)-4-methoxypicolinamide

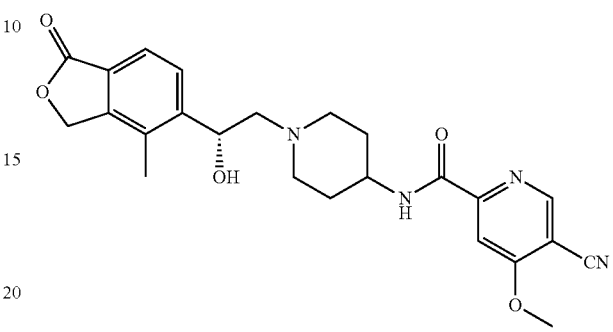

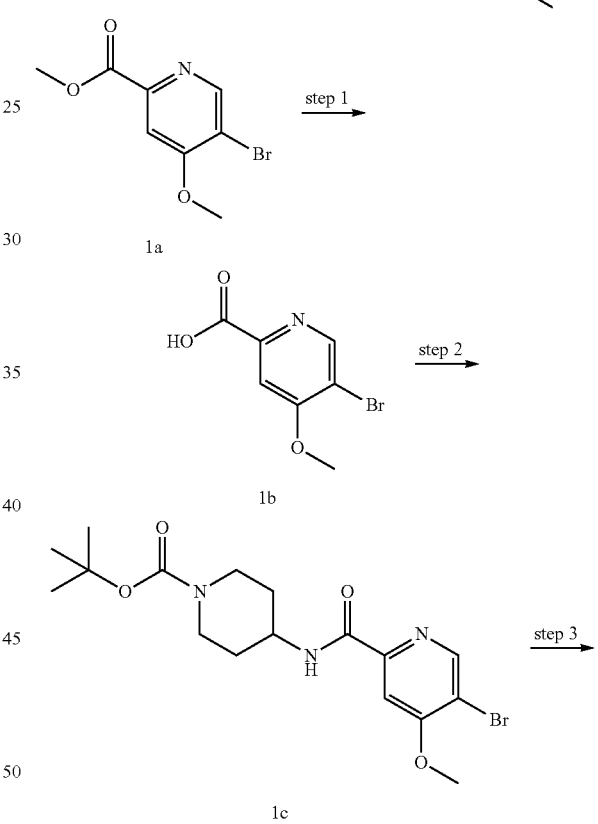

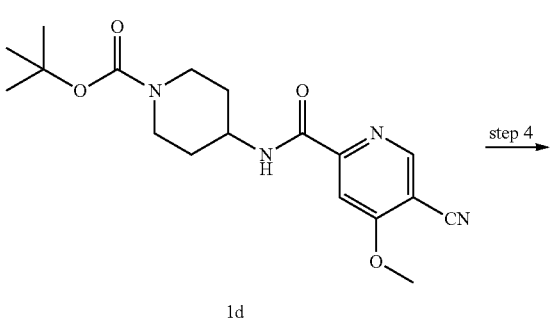

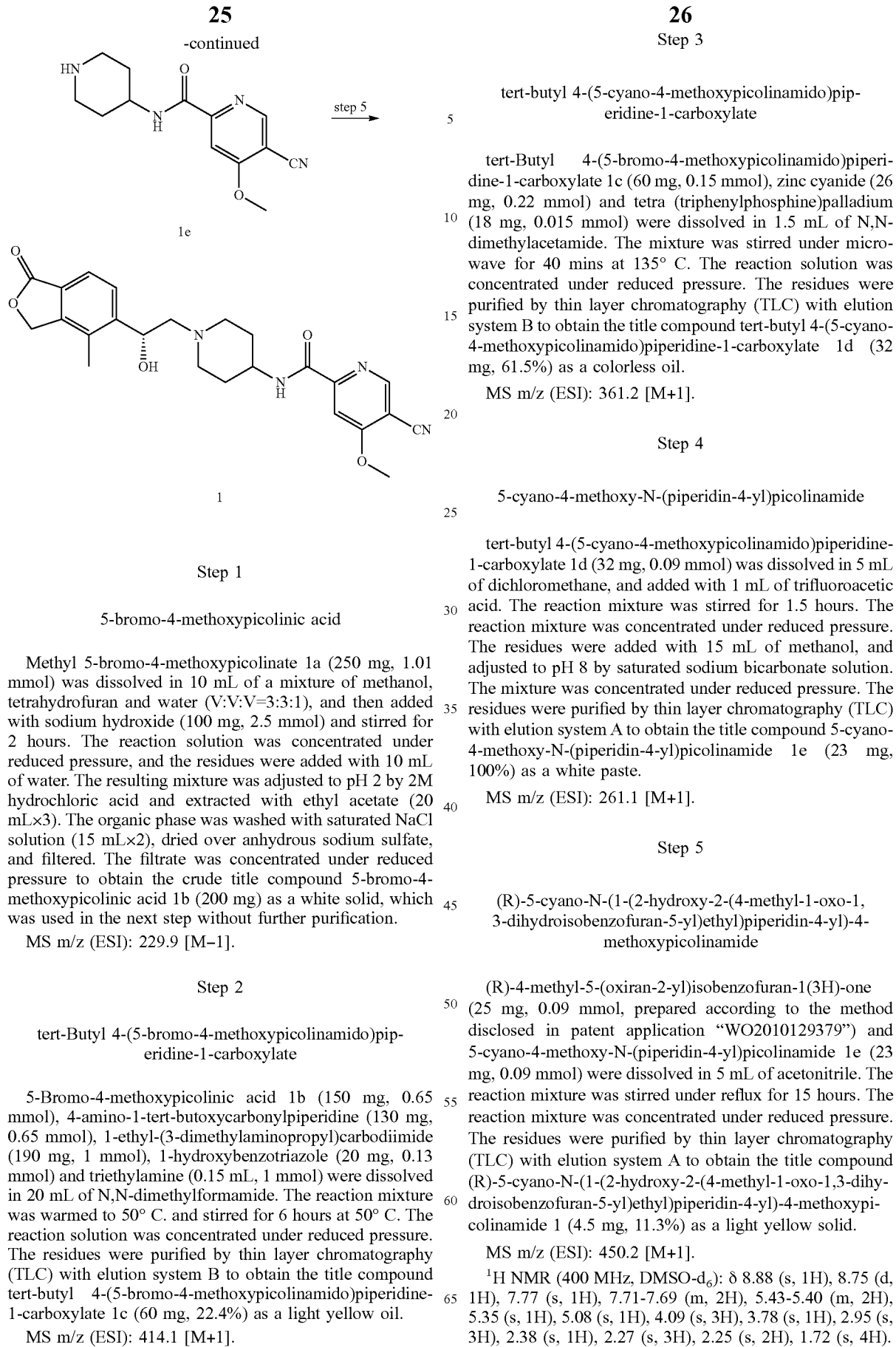

Step 1

5-bromo-4-methoxypicolinic acid

Methyl 5-bromo-4-methoxypicolinate 1a (250 mg, 1.01 mmol) was dissolved in 10 mL of a mixture of methanol, tetrahydrofuran and water (V:V:V=3:3:1), and then added with sodium hydroxide (100 mg, 2.5 mmol) and stirred for 2 hours. The reaction solution was concentrated under reduced pressure, and the residues were added with 10 mL of water. The resulting mixture was adjusted to pH 2 by 2M hydrochloric acid and extracted with ethyl acetate (20 mL×3). The organic phase was washed with saturated NaCl solution (15 mL×2), dried over anhydrous sodium sulfate, and filtered. The filtrate was concentrated under reduced pressure to obtain the crude title compound 5-bromo-4-methoxypicolinic acid 1b (200 mg) as a white solid, which was used in the next step without further purification.

MS m/z (ESI): 229.9 [M−1].

Step 2 tert-Butyl 4-(5-bromo-4-methoxypicolinamido)piperidine-1-carboxylate

5-Bromo-4-methoxypicolinic acid 1b (150 mg, 0.65 mmol), 4-amino-1-tert-butoxycarbonylpiperidine (130 mg, 0.65 mmol), 1-ethyl-(3-dimethylaminopropyl)carbodiimide (190 mg, 1 mmol), 1-hydroxybenzotriazole (20 mg, 0.13 mmol) and triethylamine (0.15 mL, 1 mmol) were dissolved in 20 mL of N,N-dimethylformamide. The reaction mixture was warmed to 50° C. and stirred for 6 hours at 50° C. The reaction solution was concentrated under reduced pressure. The residues were purified by thin layer chromatography (TLC) with elution system B to obtain the title compound tert-butyl 4-(5-bromo-4-methoxypicolinamido)piperidine-1-carboxylate 1c (60 mg, 22.4%) as a light yellow oil.

MS m/z (ESI): 414.1 [M+1].

Step 3 tert-butyl 4-(5-cyano-4-methoxypicolinamido)piperidine-1-carboxylate tert-Butyl 4-(5-bromo-4-methoxypicolinamido)piperidine-1-carboxylate 1c (60 mg, 0.15 mmol), zinc cyanide (26 mg, 0.22 mmol) and tetra (triphenylphosphine)palladium (18 mg, 0.015 mmol) were dissolved in 1.5 mL of N,N-dimethylacetamide. The mixture was stirred under microwave for 40 mins at 135° C. The reaction solution was concentrated under reduced pressure. The residues were purified by thin layer chromatography (TLC) with elution system B to obtain the title compound tert-butyl 4-(5-cyano-4-methoxypicolinamido)piperidine-1-carboxylate 1d (32 mg, 61.5%) as a colorless oil.

MS m/z (ESI): 361.2 [M+1].

Step 4

5-cyano-4-methoxy-N-(piperidin-4-yl)picolinamide tert-butyl 4-(5-cyano-4-methoxypicolinamido)piperidine-1-carboxylate 1d (32 mg, 0.09 mmol) was dissolved in 5 mL of dichloromethane, and added with 1 mL of trifluoroacetic acid. The reaction mixture was stirred for 1.5 hours. The reaction mixture was concentrated under reduced pressure. The residues were added with 15 mL of methanol, and adjusted to pH 8 by saturated sodium bicarbonate solution. The mixture was concentrated under reduced pressure. The residues were purified by thin layer chromatography (TLC) with elution system A to obtain the title compound 5-cyano-4-methoxy-N-(piperidin-4-yl)picolinamide 1e (23 mg, 100%) as a white paste.

MS m/z (ESI): 261.1 [M+1].

Step 5

(R)-5-cyano-N-(1-(2-hydroxy-2-(4-methyl-1-oxo-1,3-dihydroisobenzofuran-5-yl)ethyl)piperidin-4-yl)-4-methoxypicolinamide (R)-4-methyl-5-(oxiran-2-yl)isobenzofuran-1(3H)-one (25 mg, 0.09 mmol, prepared according to the method disclosed in patent application "WO2010129379") and 5-cyano-4-methoxy-N-(piperidin-4-yl)picolinamide 1e (23 mg, 0.09 mmol) were dissolved in 5 mL of acetonitrile. The reaction mixture was stirred under reflux for 15 hours. The reaction mixture was concentrated under reduced pressure. The residues were purified by thin layer chromatography (TLC) with elution system A to obtain the title compound (R)-5-cyano-N-(1-(2-hydroxy-2-(4-methyl-1-oxo-1,3-dihydroisobenzofuran-5-yl)ethyl)piperidin-4-yl)-4-methoxypicolinamide 1 (4.5 mg, 11.3%) as a light yellow solid.

MS m/z (ESI): 450.2 [M+1].

$^1$H NMR (400 MHz, DMSO-$d_6$): δ 8.88 (s, 1H), 8.75 (d, 1H), 7.77 (s, 1H), 7.71-7.69 (m, 2H), 5.43-5.40 (m, 2H), 5.35 (s, 1H), 5.08 (s, 1H), 4.09 (s, 3H), 3.78 (s, 1H), 2.95 (s, 3H), 2.38 (s, 1H), 2.27 (s, 3H), 2.25 (s, 2H), 1.72 (s, 4H).

Example 2

(R)-5-cyano-4-ethoxy-N-(1-(2-hydroxy-2-(4-methyl-1-oxo-1,3-dihydroisobenzofuran-5-yl)ethyl)piperidin-4-yl)picolinamide

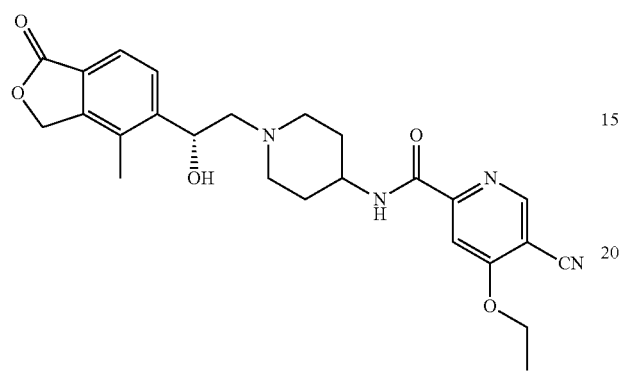

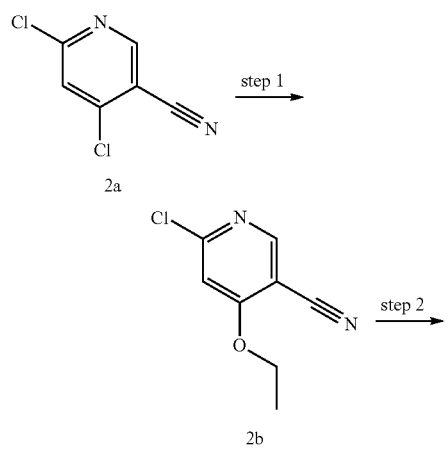

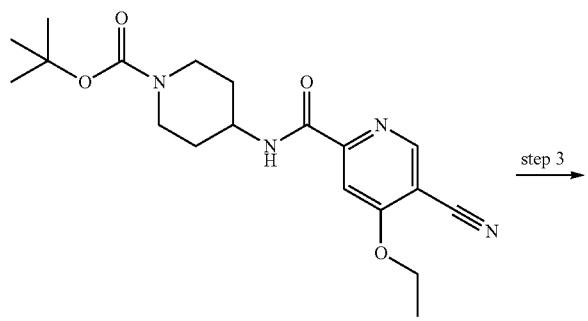

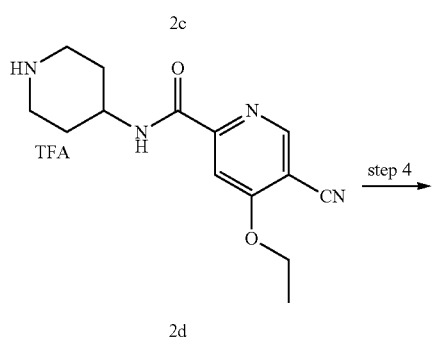

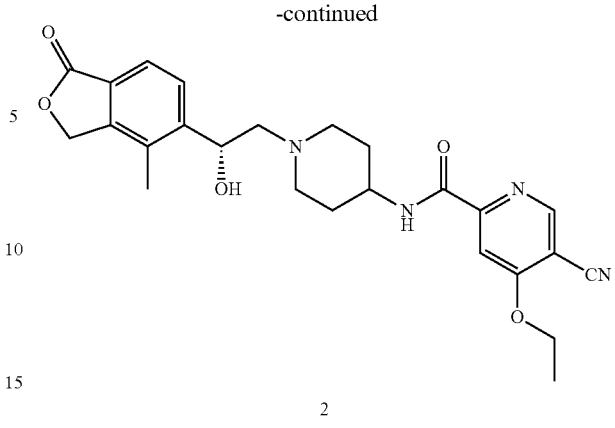

2

Step 1

6-chloro-4-ethoxynicotinonitrile 4,6-Dichloronicotinonitrile 2a (500 mg, 2.89 mmol) was dissolved in 20 mL of tetrahydrofuran, and added dropwise with 10 mL of a solution of sodium ethoxide (197 mg, 2.89 mmol) in ethanol under 0° C. The reaction mixture was warmed to room temperature and further stirred for 1 hour. The reaction mixture was concentrated under reduced pressure. The residues were purified by thin layer chromatography (TLC) with elution system B to obtain the title compound 6-chloro-4-ethoxynicotinonitrile 2b (375 mg, 71%) as a white solid.

MS m/z (ESI): 183.1 [M+1].

Step 2 tert-butyl 4-(5-cyano-4-ethoxypicolinamido)piperidine-1-carboxylate

6-Chloro-4-ethoxynicotinonitrile 2b (375 mg, 2.05 mmol), 4-amino-1-tert-butoxy-carbonylpiperidine (422 mg, 2.05 mmol), palladium acetate (23 mg, 0.1 mmol), 1,3-bis(diphenylphosphino)propane (42 mg, 0.1 mmol), triethylamine (0.57 mL, 4.1 mmol) and 20 mL of acetonitrile were charged in an autoclave. The resulting mixture was subjected to a reaction for 16 hours at 80° C. under 10 bar carbon monoxide. The reaction mixture was filtered. The filtrate was concentrated under reduced pressure. The residues were purified by thin layer chromatography (TLC) with elution system A to obtain the title compound tert-butyl 4-(5-cyano-4-ethoxypicolinamido)piperidine-1-carboxylate 2c (645 mg, 84%) as a white solid.

MS m/z (ESI): 373.2 [M−1].

Step 3

5-cyano-4-ethoxy-N-(piperidin-4-yl)picolinamide 2,2,2-trifluoroacetate tert-Butyl 4-(5-cyano-4-ethoxypicolinamido)piperidine-1-carboxylate 2c (100 mg, 0.27 mmol) was dissolved in 5 mL of dichloromethane, and added with 1 mL of trifluoroacetic acid. The reaction mixture was stirred for 1 hour. The reaction mixture was concentrated under reduced pressure to obtain the crude title compound 5-cyano-4-ethoxy-N-(piperidin-4-yl)picolinamide 2,2,2-trifluoroacetate 2d (110 mg) as a yellow oil, which was used in the next step without further purification.

Step 4

(R)-5-cyano-4-ethoxy-N-(1-(2-hydroxy-2-(4-methyl-1-oxo-1,3-dihydroisobenzofuran-5-yl)ethyl)piperidin-4-yl)picolinamide (R)-4-Methyl-5-(oxiran-2-yl)isobenzofuran-1(3H)-one (50.7 mg, 0.27 mmol) and crude 5-cyano-4-ethoxy-N-(piperidin-4-yl)picolinamide 2,2,2-trifluoroacetate 2d (110 mg, 0.27 mmol) were dissolved in 15 mL of acetonitrile and added with sodium carbonate (56.6 mg, 0.53 mmol). The reaction mixture was warmed to 80° C. and stirred for 48 hours. The reaction mixture was filtered and concentrated under reduced pressure. The residues were purified by thin layer chromatography (TLC) with elution system A to obtain the title compound (R)-5-cyano-4-ethoxy-N-(1-(2-hydroxy-2-(4-methyl-1-oxo-1,3-dihydroisobenzofuran-5-yl)ethyl)piperidin-4-yl)picolinamide 2 (50 mg, 40%) as a light yellow solid.

MS m/z (ESI): 465.2 [M+1].

$^1$H NMR (400 MHz, CD$_3$OD): δ 8.89 (s, 1H), 8.74 (d, 1H), 7.73 (s, 1H), 7.65 (s, 2H), 5.41 (d, 2H), 5.09 (br, 1H), 4.41 (d, 2H), 3.71-3.85 (m, 2H), 2.95 (br, 2H), 2.41-2.55 (m, 2H), 2.31 (s, 3H), 2.12-2.27 (m, 2H), 1.57-1.81 (m, 4H), 1.40 (t, 3H).

Example 3

(R)-5-cyano-4-(2-fluoroethoxy)-N-(1-(2-hydroxy-2-(4-methyl-1-oxo-1,3-dihydroisobenzofuran-5-yl)ethyl)piperidin-4-yl)picolinamide

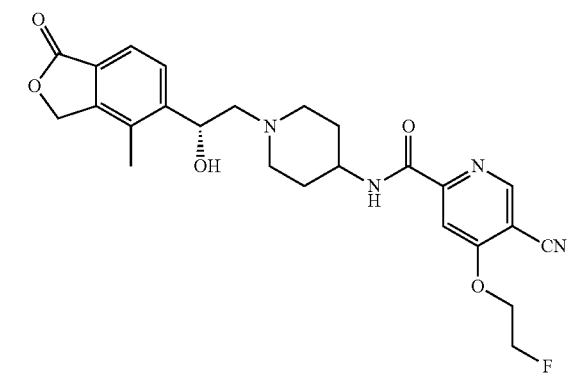

3

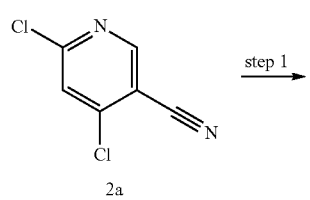

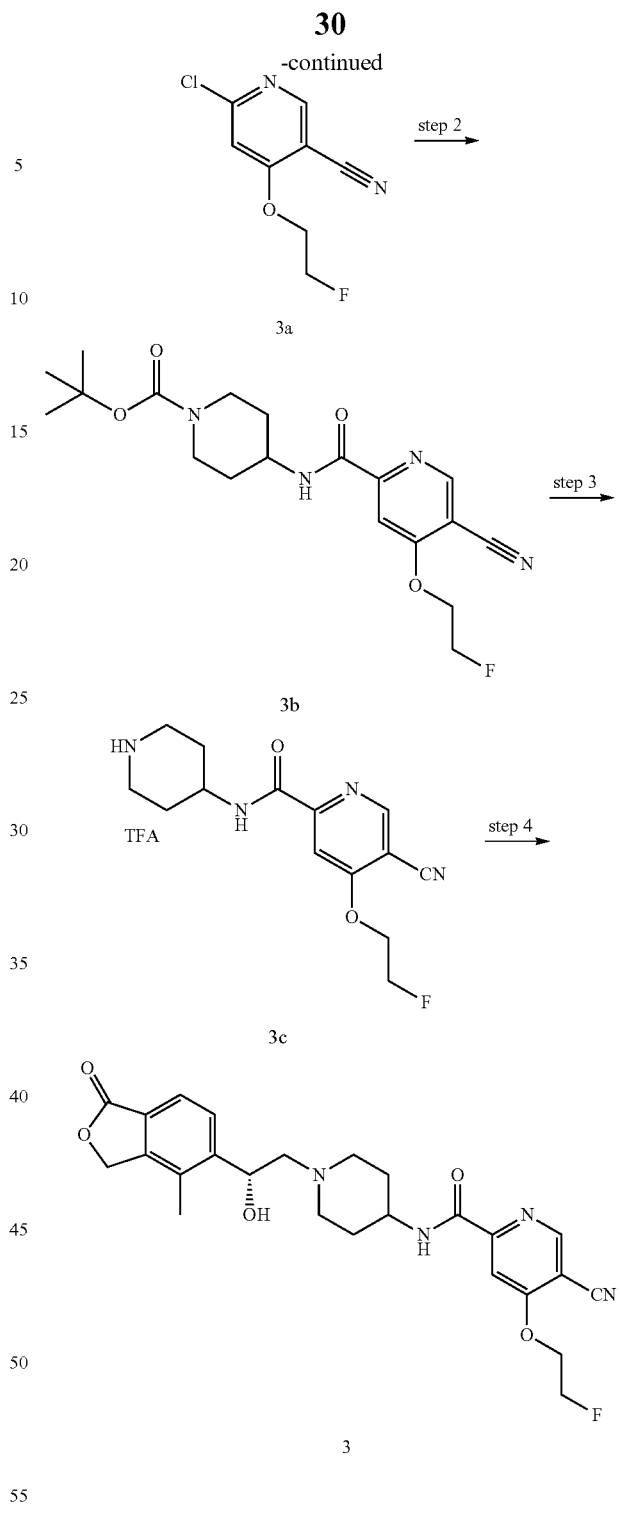

Step 1

6-chloro-4-(2-fluoroethoxy)nicotinonitrile

2-Fluoro ethanol (150 mg, 2.34 mmol) was dissolved in 10 mL of tetrahydrofuran, sodium hydride was added (281 mg, 7.02 mmol), and the resulting mixture was stirred for 1 hour. 4,6-dichloronicotinonitrile 2a (405 mg, 2.34 mmol) was dissolved in 25 mL of tetrahydrofuran, and added dropwise into the reaction mixture at 0° C. The reaction mixture was warmed to room temperature and stirred for 1 hour. The reaction mixture was quenched by 1 mL of water and concentrated under reduced pressure. The residues were purified by thin layer chromatography (TLC) with elution system B to obtain the title compound 6-chloro-4-(2-fluoroethoxy)nicotinonitrile 3a (210 mg, 45%) as a white solid.
MS m/z (ESI): 201.1 [M+1].

Step 2 tert-butyl 4-(5-cyano-4-(2-fluoroethoxy)picolinamido)piperidine-1-carboxylate

6-Chloro-4-(2-fluoroethoxy)nicotinonitrile 3a (210 mg, 1.05 mmol), 4-amino-1-tert-butoxycarbonylpiperidine (216 mg, 1.05 mmol), palladium acetate (12 mg, 0.05 mmol), 1,3-bis(diphenylphosphino)propane (22 mg, 0.05 mmol), triethylamine (0.29 mL, 2.1 mmol) and 20 mL of acetonitrile were charged in an autoclave. The resulting mixture was subjected to reaction for 16 hours at 80° C. under 10 bar carbon monoxide. The reaction mixture was filtered. The filtrate was concentrated under reduced pressure. The residues were purified by thin layer chromatography (TLC) with elution system B to obtain the title compound tert-butyl 4-(5-cyano-4-(2-fluoroethoxy)picolinamido)piperidine-1-carboxylate 3b (140 mg, 34%) as a white solid.
MS m/z (ESI): 391.1 [M−1].

Step 3

5-cyano-4-(2-fluoroethoxy)-N-(piperidin-4-yl)picolinamide 2,2,2-trifluoroacetate tert-Butyl 4-(5-cyano-4-(2-fluoroethoxy)picolinamido)piperidine-1-carboxylate 3b (70 mg, 0.18 mmol) was dissolved in 5 mL of dichloromethane, and added with 1 mL of trifluoroacetic acid. The reaction mixture was stirred for 1 hour. The reaction mixture was concentrated under reduced pressure to obtain the crude title compound 5-cyano-4-(2-fluoroethoxy)-N-(piperidin-4-yl)picolinamide 2,2,2-trifluoroacetate 3c (80 mg) as a yellow oil, which was used in the next step without further purification.

Step 4

(R)-5-cyano-4-(2-fluoroethoxy)-N-(1-(2-hydroxy-2-(4-methyl-1-oxo-1,3-dihydroisobenzofuran-5-yl)ethyl)piperidin-4-yl)picolinamide (R)-4-Methyl-5-(oxiran-2-yl)isobenzofuran-1(3H)-one (34 mg, 0.18 mmol) and crude 5-cyano-4-(2-fluoroethoxy)-N-(piperidin-4-yl)picolinamide 2,2,2-trifluoroacetate 3c (80 mg, 0.18 mmol) were dissolved in 20 mL of acetonitrile, and added with sodium carbonate (38 mg, 0.36 mmol). The reaction mixture was warmed to 80° C. and stirred for 48 hours. The reaction mixture was concentrated under reduced pressure. The residues were purified by thin layer chromatography (TLC) with elution system A to obtain the title compound (R)-5-cyano-4-(2-fluoroethoxy)-N-(1-(2-hydroxy-2-(4-methyl-1-oxo-1,3-dihydroisobenzofuran-5-yl)ethyl)piperidin-4-yl)picolinamide 3 (10 mg, 12%) as a white solid.

MS m/z (ESI): 481.2 [M−1]

$^1$H NMR (400 MHz, CD$_3$OD): δ 8.93 (s, 1H), 8.79 (d, 1H), 7.82 (s, 1H), 7.71 (d, 2H), 5.41 (d, 2H), 5.14 (br, 1H), 4.89 (t, 1H), 4.77 (t, 1H), 4.72 (t, 1H), 4.65 (t, 1H), 3.71-3.82 (m, 2H), 2.85-3.15 (m, 2H), 2.40-2.54 (m, 2H), 2.31 (s, 3H), 2.12-2.26 (m, 2H), 1.61-1.90 (m, 4H).

Example 4

(R)-5-cyano-4-(difluoromethoxy)-N-(1-(2-hydroxy-2-(4-methyl-1-oxo-1,3-dihydroisobenzofuran-5-yl)ethyl)piperidin-4-yl)picolinamide

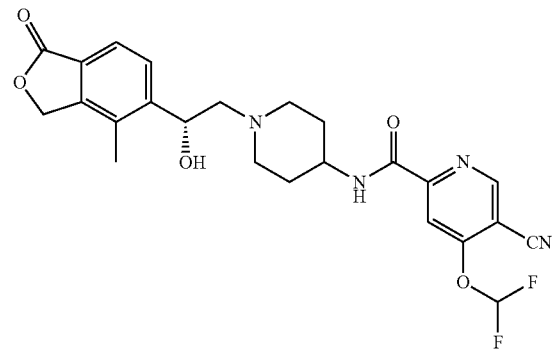

4

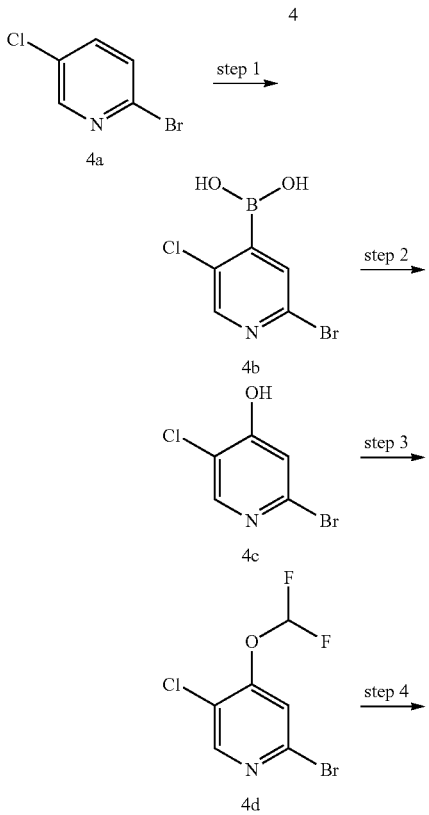

-continued

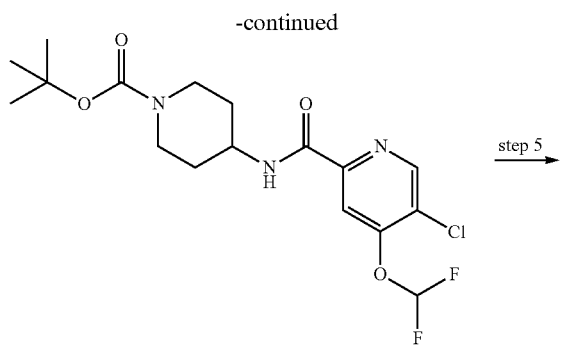

further stirred for 16 hours. 50 mL of 4% sodium hydroxide solution was added. The mixture was stirred for 30 mins. The aqueous phase was separated and adjusted to pH 3 to 4 by 6 M sodium hydroxide solution in an ice-water bath. Then, the aqueous phase was extracted with ethyl acetate (50 mL×2). The organic phases were combined, dried over anhydrous sodium sulfate and filtered. The filtrate was concentrated under reduced pressure to obtain the crude title compound (2-bromo-5-chloropyridin-4-yl)boronic acid 4b (1.3 g, 53%) as a white solid.

Step 2

2-bromo-5-chloropyridin-4-ol (2-Bromo-5-chloropyridin-4-yl)boronic acid 4b (1.3 g, 5.51 mmol) was dissolved in 40 mL of dichloromethane, and added with hydrogen peroxide (1.87 mL, 16.5 mmol). The resulting mixture was stirred for 16 hours. The reaction mixture was concentrated under reduced pressure to obtain the crude title compound 2-bromo-5-chloropyridin-4-ol 4c (1 g, 88%) as a white solid.

MS m/z (ESI): 205.9/207.9 [M+1].

Step 3

2-bromo-5-chloro-4-(difluoromethoxy)pyridine

The crude 2-bromo-5-chloropyridin-4-ol 4c (320 mg, 1.54 mmol), sodium 2-chloro-2,2-difluoroacetate (470 mg, 3.08 mmol) and potassium carbonate (470 mg, 3.39 mmol) were dissolved in 5 mL of N,N-dimethylacetamide. The reaction mixture was warmed to 120° C. and stirred for 1 hour under microwave. The reaction mixture was concentrated under reduced pressure. The residues were purified by thin layer chromatography (TLC) with elution system B to obtain the title compound 2-bromo-5-chloro-4-(difluoromethoxy)pyridine 4d (950 mg, 60%) as a colourless oil.

Step 4 tert-butyl 4-(5-chloro-4-(difluoromethoxy)picolinamido)piperidine-1-carboxylate

2-Bromo-5-chloro-4-(difluoromethoxy)pyridine 4d (1.03 g, 3.99 mmol), 4-amino-1-tert-butoxycarbonylpiperidine (800 mg, 3.99 mmol), palladium acetate (45 mg, 0.2 mmol), 1,3-bis(diphenylphosphino)propane (82 mg, 0.2 mmol), triethylamine (1.1 mL, 7.98 mmol) and 30 mL of acetonitrile were charged in an autoclave. The resulting mixture was reacted for 16 hours at 80° C. under 10 bar carbon monoxide. The reaction mixture was filtered. The filtrate was concentrated under reduced pressure. The residues were purified by thin layer chromatography (TLC) with elution system B to obtain the title compound tert-butyl 4-(5-chloro-4-(difluoromethoxy)picolinamido)piperidine-1-carboxylate 4e (809 mg, 50%) as a white solid.

MS m/z (ESI): 404.1 [M−1].

Step 1

(2-bromo-5-chloropyridin-4-yl)boronic acid

2-Bromo-5-chloropyridine 4a (2 g, 10.4 mmol) was dissolved in 40 mL of tetrahydrofuran, and then added dropwise with 7.8 mL of 2M lithium diisopropylamide under −78° C. The resulting mixture was stirred for 1 hour. Triisopropyl borate (2.94 mg, 15.6 mmol) was added and the reaction mixture was stirred for 30 mins at −78° C. The reaction mixture was then warmed to room temperature and Step 5 tert-butyl 4-(5-cyano-4-(difluoromethoxy)picolinamido) piperidine-1-carboxylate tert-Butyl 4-(5-chloro-4-(difluoromethoxy)picolinamido)piperidine-1-carboxylate 4e (100 mg, 0.25 mmol), zinc cyanide (57.6 mg, 0.49 mmol) and tetra (triphenylphosphine)palladium (88 mg, 0.07 mmol) were dissolved in 5 mL of N,N-dimethylacetamide. The mixture was stirred under microwave for 30 mins at 170° C. The reaction solution was concentrated under reduced pressure. The residues were purified by thin layer chromatography (TLC) with elution system B to obtain the title compound tert-butyl 4-(5-cyano-4-(difluoromethoxy)picolinamido)piperidine-1-carboxylate 4f (83 mg, 85%) as a white solid.

MS m/z (ESI): 395.0 [M−1].

Step 6

5-cyano-4-(difluoromethoxy)-N-(piperidin-4-yl)picolinamide 2,2,2-trifluoroacetate tert-Butyl 4-(5-cyano-4-(difluoromethoxy)picolinamido)piperidine-1-carboxylate 4f (250 mg, 0.63 mmol) was dissolved in 5 mL of dichloromethane, and added with 2 mL of trifluoroacetic acid. The reaction mixture was stirred for 1 hour. The reaction mixture was concentrated under reduced pressure to obtain the crude title compound 5-cyano-4-(difluoromethoxy)-N-(piperidin-4-yl)picolinamide 2,2,2-trifluoroacetate 4g (540 mg) as a yellow oil, which was used in the next step without further purification.

MS m/z (ESI): 297.2 [M+1].

Step 7

(R)-5-cyano-4-(difluoromethoxy)-N-(1-(2-hydroxy-2-(4-methyl-1-oxo-1,3-dihydroisobenzofuran-5-yl)ethyl)piperidin-4-yl)picolinamide (R)-4-Methyl-5-(oxiran-2-yl)isobenzofuran-1(3H)-one (57.7 mg, 0.3 mmol), crude 5-cyano-4-(difluoromethoxy)-N-(piperidin-4-yl)picolinamide 2,2,2-trifluoroacetate 4g (260 mg, 0.3 mmol) and N,N-diisopropylethylamine (78.4 mg, 0.61 mmol) were dissolved in 3 mL of ethanol. The reaction mixture was warmed to 135° C. and stirred for 1 hour under microwave. The reaction mixture was concentrated under reduced pressure. The residues were purified by thin layer chromatography (TLC) with elution system A to obtain the title compound (R)-5-cyano-4-(difluoromethoxy)-N-(1-(2-hydroxy-2-(4-methyl-1-oxo-1,3-dihydroisobenzofuran-5-yl)ethyl)piperidin-4-yl)picolinamide 4 (30 mg, 20%) as a white solid.

MS m/z (ESI): 487.2 [M+1]
$^1$H NMR (400 MHz, CD$_3$OD): δ 9.13 (s, 1H), 8.87 (d, 1H), 7.98 (t, 1H), 7.83 (s, 1H), 7.63-7.78 (m, 2H), 5.40 (d, 2H), 5.08 (br, 1H), 3.70-3.81 (m, 2H), 2.96 (br, 2H), 2.40-2.54 (m, 2H), 2.28 (s, 3H), 2.11-2.26 (m, 2H), 1.61-1.75 (m, 4H).

Test Examples

Biological Assay

Test Example 1: The Inhibitory Activity of the Present Compounds on Human ROMK and Rat ROMK Channels The method described hereafter was used for determining the inhibitory activity of the present compounds on human ROMK and rat ROMK channels.
1. Materials and Instruments
(1) FluxOR™ potassium ion channel assay (F10016, Invitrogen)
(2) Ouabain (O3125-1G, Sigma)
(3) FlexStation3 microplate reader (Molecular Devices)
(4) Human ROMK/HEK293 cell: HEK293 cell line stably expressing the ROMK channel transfected by human ROMK cDNA (NCBI SEQ ID NO. NM-000220.4)
(5) Rat ROMK/HEK293 cell: HEK293 cell line transfected by rat ROMK cDNA (NCBI SEQ ID NO. NM-017023.1) stably expressing the ROMK channel
(6) HEK293 cell line: Cell Bank of Chinese Academy of Sciences, GNHu43
2. Experimental Procedure Except for ddH$_2$O and Ouabain, all of the experimental reagents are from FluxOR™ Potassium Ion Channel Assay Kit and the formulation methods also refer to the kit instructions.
(1) Human ROMK/HEK293 cell was seeded on PDL (Poly-D-lysine) coated plates at 20000 cells/well on the previous day;
(2) After overnight culture, the plate medium was discarded; then according to the Fluxor™ Potassium Ion Channel Assay Kit instructions, the dye was added at 100 μL/hole, and then incubated for 90 mins at room temperature;
(3) The dye was then decanted and 1004, of assay buffer containing ouabain (30004) and probenecid were added in each well;
(4) 1 μL of compound or DMSO was added to the corresponding wells, shocked for 30 seconds, and incubated for 30 mins at room temperature;
(5) The plates were placed in a FlexStation3 microplate reader, and then added with stimulation buffer (K$_2$SO$_4$: Tl$_2$SO$_4$: 1×FluxOR Chloride-free Buffer: ddH$_2$O=3:12:40:125) at 25 μL/well, then the value was read continuously for 5 mins at EX/EM of 490/525 nm immediately; and
(6) The IC$_{50}$ of the present compounds on human ROMK channel was obtained by data processing software Graphpad.

The above procedures were repeated, except for replacing human ROMK/HEK293 cells with rat ROMK/HEK 293 cells, to determine the inhibition IC$_{50}$ of the present compounds on rat ROMK channel.

The inhibitory activity of the present compounds on human ROMK or rat ROMK channel was tested by the assay described above. The IC$_{50}$ values are shown in Table 1 below.

TABLE 1

The inhibitory IC$_{50}$ of the present compounds on human ROMK or rat ROMK channels

| Example No. | Human ROMK IC$_{50}$ (nM) | Rat ROMK IC$_{50}$ (nM) |
|---|---|---|
| 1 | 40 | 192 |
| 2 | 28 | 89 |

Conclusion: The compounds of the present invention have significant inhibitory activity on human ROMK and rat ROMK channels.

Test Example 2: The Inhibitory Activity of the Present Compounds on hERG

The method described hereafter is used for determining the inhibitory activity of the present compounds on hERG
1. Materials and Instruments
(1) FluxOR™ potassium ion channel assay (F10016, invitrogen)
(2) FlexStation3 microplate reader (molecular devices)

(3) hERG/HEK293 cell: HEK293 cell line stably expressing the hERG channel transfected by hERG cDNA (NCBI SEQ ID NO. NM-000238(RC215928, origene)).

2. Experimental Procedure

Except for ddH$_2$O, all of the experimental reagents are from FluxOR™ Potassium Ion Channel Assay Kit and the formulation methods also refer to the kit instructions.

(1) Human hERG/HEK293 cell was seeded on PDL (Poly-D-lysine) coated plates at 25000 cells/well on the previous day;

(2) After overnight culture, the plate medium was discarded; then according to FluxOR™ potassium ion channel detection requirements operation, the dye was added at 100 μL/hole, and then incubated for 90 mins at room temperature;

(3) The dye was then decanted and 100 μL of assay buffer containing 1004, probenecid were added in each well;

(4) 1 μL of compound or DMSO was added to the corresponding wells, shocked for 30 seconds, and incubated for 30 mins at room temperature;

(5) The plates were placed in a FlexStation3 microplate reader, and then added with stimulation buffer (K$_2$SO$_4$: Tl$_2$SO$_4$: 1×FluxOR Chloride-free Buffer: ddH$_2$O=2:1:2:5) at 25 μL/well, then the value was read continuously for 5 mins at EX/EM of 490/525 nm immediately; and (6) The IC$_{50}$ of the present compounds on human hERG ion channel was obtained by data processing software Graphpad.

The inhibitory activity of the present compounds on hERG was tested by the assay described above. The IC$_{50}$ values are shown in Table 2 below.

TABLE 2

| The inhibitory IC$_{50}$ of the present compounds on hERG | |
|---|---|
| Example No. | hERG IC$_{50}$ (μM) |
| 1 | 43.7 |

Conclusion: The compounds of the present invention have a weak inhibitory effect on hERG, which indicates that the compounds of the present invention have a low cardiotoxicity.

Test Example 3: The Effect of the Electrophysiological Manual Patch Clamp on ROMK Potassium Channel 1. Protocol The experiment was designed to test the effect of compounds on ROMK potassium channel in HEK 293 in vitro. ROMK potassium channel is stably expressed on the HEK293 cells of the present application. After the potassium ion current was stabilized, the effect of the present compound on the potassium channel was obtained by comparing the potassium current obtained before and after the use of the present compound at different concentrations.

2. Materials and Instruments (1) HEK293 cell line: cell bank of Chinese academy of sciences, GNHu43;

(2) Human ROMK/HEK293 cell: HEK293 cell line stably expressing the ROMK channel transfected by human ROMK cDNA (NCBI SEQ ID NO. NM-000220.4);

(3) Extracellular fluid (mM): NaCl, 137; KCl, 4; CaCl$_2$, 1.8; MgCl$_2$, 1; HEPES, 10; glucose, 10; pH 7.4 (NaOH titration); and (4) Intracellular fluid (mM): K Aspartate, 130; MgCl$_2$, 5; EGTA 5; HEPES, 10; Tris-ATP, 4; pH 7.2 (KOH titration).

The compounds were purchased from Sigma (St. Louis, Mo.) in addition to NaOH and KOH for acid-base titration.

Cell culture medium: Ham's F12 medium (Invitrogen), 10% (v/v) inactivated fetal bovine serum, 100 μg/mL hygromycin B, 100 μg/mL Geneticin;

Manual patch clamp system: HEKA EPC-10 signal amplifier and digital conversion system, purchased from Germany HEKA Electronics;

Micro-control instruments: MP-225; and

Drawing electrode instrument: PC-10 (Narishige, Japan).

3. Experimental Procedure

Test compounds were dissolved in dimethyl sulfoxide (DMSO) and then stocked at room temperature. On the day of the experiment, test compounds were diluted to the following final concentration (3, 10, 30, 100, 300 nM) using extracellular fluid. The final concentration of the test compounds in DMSO was 0.3%.

Human ROMK/HEK293 cells were grown in a culture dish containing the above-mentioned cell culture medium and cultured in an incubator containing 5% CO$_2$ at 37° C. Human ROMK/HEK293 cells were transferred to a round glass plate placed in the culture dish 24 to 48 hours before the experiment, and grown under the same culture medium and conditions as above. The human ROMK/HEK293 cells on each of the round glass plates were required to reach a density in which the vast majority of cells was independent and individual.

A manual patch clamp system was used for whole-cell current record in this experiment. The round glass plate with human ROMK/HEK293 cells grown on the surface was placed in an electrophysiological recording bath under an inverted microscope. The recording bath was maintained under continuous perfusion with extracellular fluid (approximately 1 mL per minute). The whole-cell patch clamp current recording technique was applied in the experiment. Unless otherwise stated, the tests were carried out at room temperature (~25° C.). Cells were clamped at −80 mV. The cell clamp voltage was depolarized to +20 mV for 5 seconds to activate the ROMK potassium channel, and then clamped to −50 mV to eliminate inactivation and generate tail current. The tail current peak value was used as the value of the ROMK current. After the ROMK potassium current recorded in the above steps was stabilized under continuous perfusion with extracellular liquid in the recording bath, the drug to be tested was perfused until the inhibition of the drug on the ROMK current reached a steady state. Generally, the reclosing of three consecutive current recording lines was used as the criteria for determining a stable state. After stabilization, the cells were perfused with extracellular fluid until the ROMK current returned to the value before the addition of the drug. One cell can be tested for one or more drugs, or for multiple concentrations of the same drug, but needs to be rinsed with extracellular fluid between different drugs.

4. Data Analysis

The data were analyzed by HEKA Patchmaster, XLFit and Graphpad Prism data analysis software. The IC$_{50}$ values are shown in Table 3 below.

TABLE 3

| The inhibitory IC$_{50}$ of the present compounds on ROMK potassium channel | |
|---|---|
| Example No. | IC$_{50}$ (nM) |
| 1 | 18.7 |

Conclusion: The compounds of the present invention have a strong inhibitory effect on ROMK potassium channel.

Test Example 4: The Effect on hERG Potassium Channel Determined by Electrophysiological Manual Patch Clamp 1. Object The object of this experiment is to test the effect of compounds on hERG potassium channel of CHO cells in vitro. In this present invention, hERG potassium channel is stably expressed on the CHO cells. After potassium ion current was stabilized, the effect of the compound on the potassium channel was obtained by comparing the magnitude of potassium current before and after application of different compound concentrations.

1. Materials and Instruments (1) CHO cell line: Sophion Biosciense Company Denmark;
(2) hERG/CHO cell: CHO cell line stably expressing the hERG channel transfected human ROMK cDNA (NCBI SEQ ID NO. NM-000238 (RC215928, origene));
(3) Extracellular fluid (mM): EC 0.0.0 NaCl-Ringer's solution, NaCl, 145; KCl, 4; $CaCl_2$, 2; $MgCl_2$, 1; HEPES, 10; glucose, 10; pH 7.4 (NaOH titration), osmotic pressure ~305 mOsm; and
(4) Intracellular fluid (mM): IC 0.0.0 KCl-Ringer's solution, KCl, 120; $CaCl_2$, 5.374; $MgCl_2$, 1.75; EGTA 5; HEPES, 10; Na-ATP 4; pH 7.25 (KOH titration), osmotic pressure ~305 mOsm.

The compounds were purchased from Sigma (St. Louis, Mo.) in addition to NaOH and KOH for acid-base titration. Cell culture medium: Ham's F12 medium (Invitrogen), 10% (v/v) inactivated fetal bovine serum, 100 μg/mL hygromycin B, 100 μg/mL Geneticin;
Manual patch clamp system: HEKA EPC-10 signal amplifier and digital conversion system, purchased from Germany HEKA Electronics;
Micro-control instruments: MP-225; and
Drawing electrode instrument: PC-10 (Narishige, Japan).

2. Experimental Procedure

The test compounds were gradiently diluted with dimethyl sulfoxide (DMSO) to 30, 10, 3, 1, 0.3 and 0.1 mM and then stocked at room temperature beforehand. Then, the stock solution was diluted to the following final concentrations (30, 10, 3, 1, 0.3 and 0.1 μM) using extracellular fluid. The final concentration of the test compound in DMSO was 0.1%. All stock solutions and test solutions were ultrasonically oscillated for 5-10 minutes to ensure complete dissolution of the compounds.

CHO hERG cells were grown in a culture dish containing the above-mentioned cell culture medium and cultured in an incubator containing 5% $CO_2$ at 37° C. CHO hERG cells were transferred to round glass plates placed in the culture dish 24 to 48 hours before the experiment and grown under the same culture medium and conditions as above. The CHO hERG cells on each of the round glass plates were required to reach a density in which the vast majority of cells was independent and individual.

A manual patch clamp system was used for whole-cell current record in this experiment. The round glass plate with CHO hERG cells grown on the surface was placed in an electrophysiological recording bath under an inverted microscope. The recording bath was maintained under continuous perfusion with extracellular fluid (approximately 1 mL per minute). The whole-cell patch clamp current recording technique was applied in the experiment. Unless otherwise stated, the tests were carried out at room temperature (~25° C.). Cells were clamped at −80 mV. The cell clamp voltage was depolarized to +20 mV for 5 seconds to activate the hERG potassium channel, and then clamped to −50 mV to eliminate inactivation and generate tail current. The tail current peak value was used as the value of the hERG current. After the hERG potassium current recorded in the above steps was stabilized under continuous perfusion with extracellular liquid in the recording bath, the drug to be tested was perfused until the inhibition of the drug on the hERG current reached a steady state. Generally, the reclosing of three consecutive current recording lines was used as the criteria for determining a stable state, After stabilization, the cells were perfused with extracellular fluid until the hERG current returned to the value before the addition of the drug. One cell can be tested for one or more drugs, or for multiple concentrations of the same drug, but need to be rinsed with extracellular fluid between different drugs.

4. Data Analysis

The data were analyzed by HEKA Patchmaster, XLFit and Graphpad Prism data analysis software. The $IC_{50}$ values are shown in Table 4 below.

TABLE 4

| The inhibitory $IC_{50}$ of the present compounds on hERG potassium channel | |
|---|---|
| Example No. | $IC_{50}$ (μM) |
| 1 | 14.95 |

Conclusion: The compounds of the present invention have a weak inhibitory effect on hERG potassium channel, which indicates that the compounds of the present invention have a low cardiotoxicity.

Test Example 5: The Pharmacokinetics Assay of the Present Compounds

1. Abstract

Rats were used as test animals. The drug concentration in plasma at different time points was determined by LC/MS/MS after administration of the compounds to rats. The pharmacokinetic behavior of the present compounds was studied and evaluated in rats.

2. Protocol 2.1 Samples

Compounds of Example 1

2.2 Test Animals

Four (4) healthy adult Sprague-Dawley (SD) rats, half male and half female, were purchased from SINO-BRITSH SIPPR/BK LAB. ANIMAL LTD., CO, with Certificate No.: SCXK (Shanghai) 2008-0016.

2.3 Preparation of the Test Compounds

The appropriate amount of the test compounds was weighed, and added with 0.5% CMC-Na to a final volume to prepare a 0.5 mg/mL suspension by ultrasonication.

2.4 Administration

Following fasting overnight, 4 SD rats, half male and half female were administered intragastrically a dose of 5.0 mg/kg and an administration volume of 10 mL/kg.

3. Process

Blood (0.1 mL) was sampled from orbital sinus before administration and 0.5 h, 1.0 h, 2.0 h, 4.0 h, 6.0 h, 8.0 h, 11.0 h, and 24.0 h after administration. The samples were stored in EDTA anticoagulation tubes, and centrifuged for 10 minutes at 3,500 rpm to separate the blood plasma. The plasma samples were stored at −20° C. The rats were fed 2 hours after administration.

The plasma concentration of the test compounds in rats after intragastric administration was determined by LC-MS/MS. Plasma samples were analyzed after pretreatment by protein precipitation.

4. Results of Pharmacokinetic Parameters

Pharmacokinetic parameters of the present compounds are shown in Table 5 below.

TABLE 5

| | Pharmacokinetics Parameters (5 mg/kg) | | | | | |
|---|---|---|---|---|---|---|
| Example No. 1 compound | Plasma Conc. Cmax (ng/mL) | Area Under Curve AUC (ng/mL * h) | Half-Life T½ (h) | Mean Residence Time MRT (h) | Clearance CLz/F (ml/min/kg) | Apparent Distribution Volume Vz/F (ml/kg) |
| Oral | 1329 ± 388 | 9283 ± 3046 | 3.62 ± 0.33 | 5.51 ± 0.75 | 9.82 ± 3.50 | 3019 ± 841 |

Test Example 6: The Diuretic Efficacy of ROMK Inhibitors in SD Rats

1. Object

The diuretic efficacy of compound 1 and positive control drug of ROMK inhibitor on SD rats was evaluated.

2. Methods and Materials 2.1 Test Animals and Feeding Conditions

Male SD rats were purchased from SINO-BRITSH SIPPR/BK LAB. ANIMAL LTD., CO (Shanghai, China, Certificate No. 2008001647752, License SCXK (Shanghai) 2013-0016). The rats were 120-130 g, and fed at 5/cage, in a 12/12 hours light/dark cycle regulation, at a constant temperature of 23±1° C., humidity of 50~60%, and free access to water and food. The male SD rats were acclimated to this condition for 7 days before their use in the diuresis experiment.

2.2 Test Drug

Compound 1;

The structure of the positive control drug is as follows:

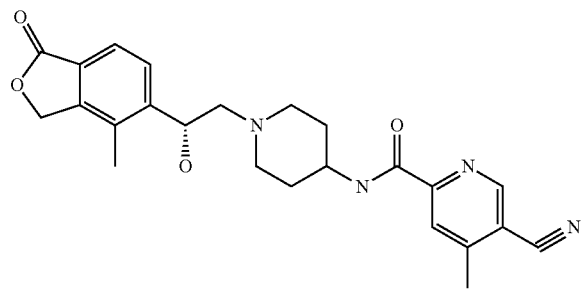 [SMILES: Cc1cc(C(=O)NC2CCN(C[C@H](O)c3ccc4c(c3C)COC4=O)CC2)ncc1C#N]

0.9% NaCl solution (500 ml: 4.5 g).
CMC Na: Batch No. 20131022, Sinopharm Group Chemical Reagent Co., Ltd.
Sodium detection kit: Batch No. 20150203, from Nanjing Jiancheng Biotechnology Company.
Potassium detection kit: Batch No. 20141112, from Nanjing Jiancheng Biotechnology Company.

The drug dose was calculated according to the tree base.

2.3 the Experimental Design and Method 2.3.1 Animal Grouping

After adaptive feeding, the animals were grouped as follows:

| Groups | n | Administration |
|---|---|---|
| Normal | 10 | 0.5% CMC (i.g.once) |
| Compound 1-0.03 mg/kg | 10 | 0.03 mg/kg (i.g.once) |
| Compound 1-0.1 mg/kg | 10 | 0.1 mg/kg (i.g.once) |
| Positive control drug −0.03 mg/kg | 10 | 0.03 mg/kg (i.g.once) |
| Positive control drug −0.1 mg/kg | 10 | 0.1 mg/kg (i.g.once) |

2.3.2 the Experiment Method

The experiment was carried out according to the method disclosed in PCT Patent Application Publication WO2010129379A1 After adaptive feeding, the rats were placed in metabolism cages and fasted overnight. The rats were weighed and randomly divided into the following groups: blank control group, compound 1 tested drug 0.03 mg/kg group and 0.1 mg/kg group, and the positive control group 0.03 mg/kg and group 0.1 mg/kg, with 10 rats for each group. Each rat was intragastrically administered each compound (ig, 1 ml/kg). The rats in the blank control group were fed with the corresponding solvent. After intragastric administration, the rats were placed in the normal cage. After 30 min, 25 ml/kg normal saline was given. Rats were put into the metabolic cages, and fasting for food and water began immediately. The total urine volume in 4 h was collected and measured. The urinary sodium and urinary potassium excretion in 4 h were also measured. The orbital serum was collected after the collection of urine to test the serum sodium and serum potassium concentrations.

2.4 the Experimental Apparatus

Room temperature centrifuge: Model 5417C, supplied by Eppendorf.

2.5 Data Representation and Statistical Processing

The experimental data were expressed as mean±standard deviation (S.D.). The data was statistically compared using the t test of excel. The data between the drug group and the control group were analyzed and compared to determine whether there was a significant statistical significance. *P<0.05 indicates that there is a significant difference between the drug group and the control group, and ** P<0.01 indicates that there is a high significant difference between the drug group and the control group.

3. Result

Figure 2:
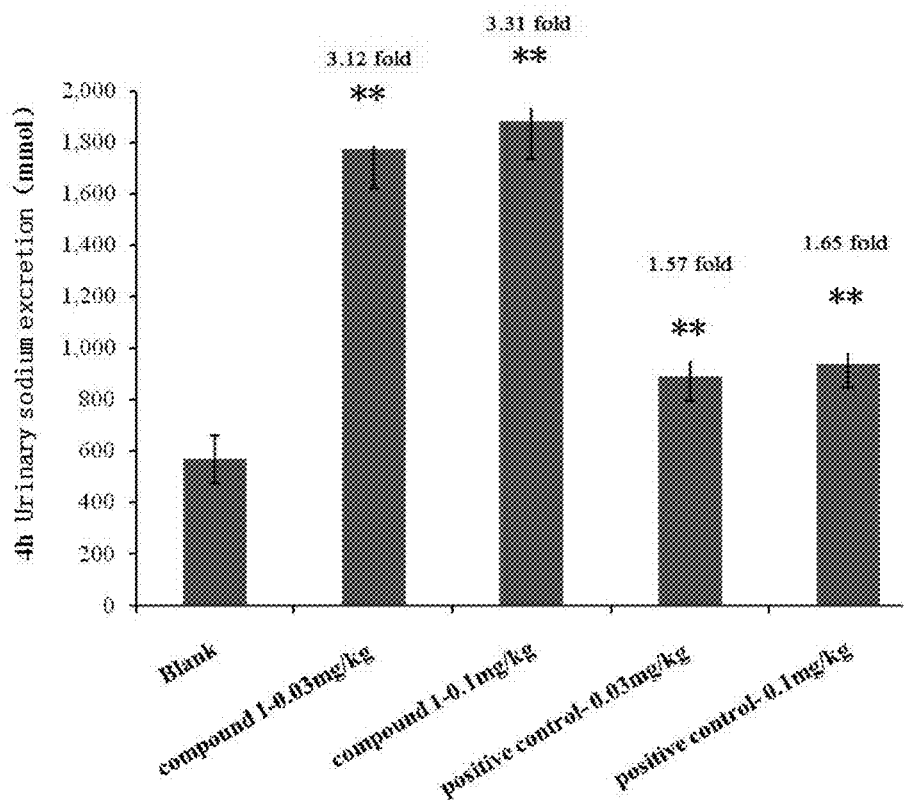
FIG. 2 shows the effect of a ROMK inhibitor on urinary sodium excretion of SD rats.
Figure 3:
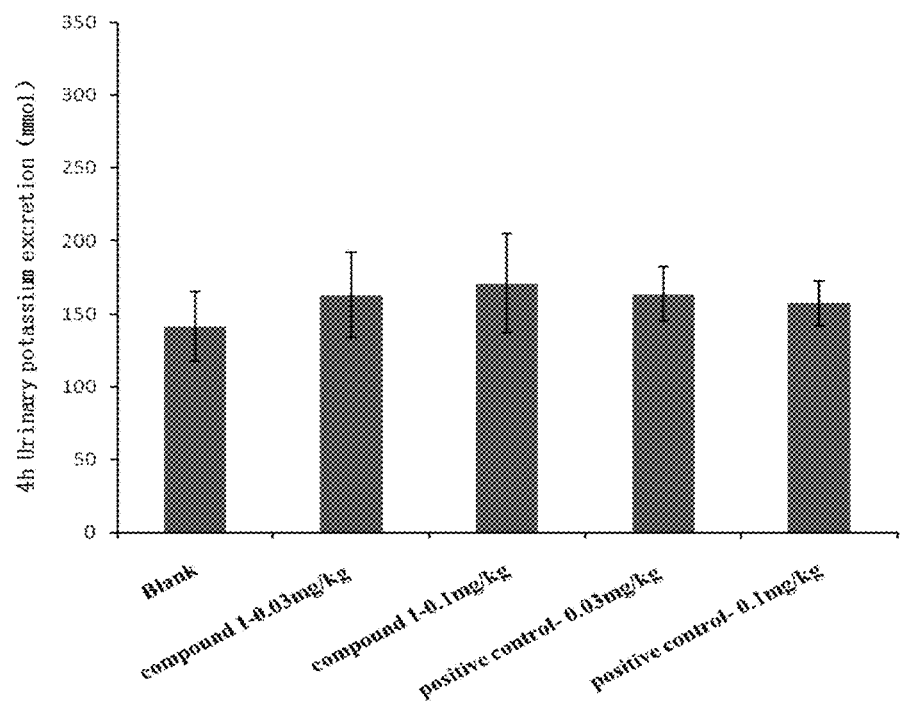
FIG. 3 shows the effect of a ROMK inhibitor on urinary potassium excretion of SD rats.
Figure 4:
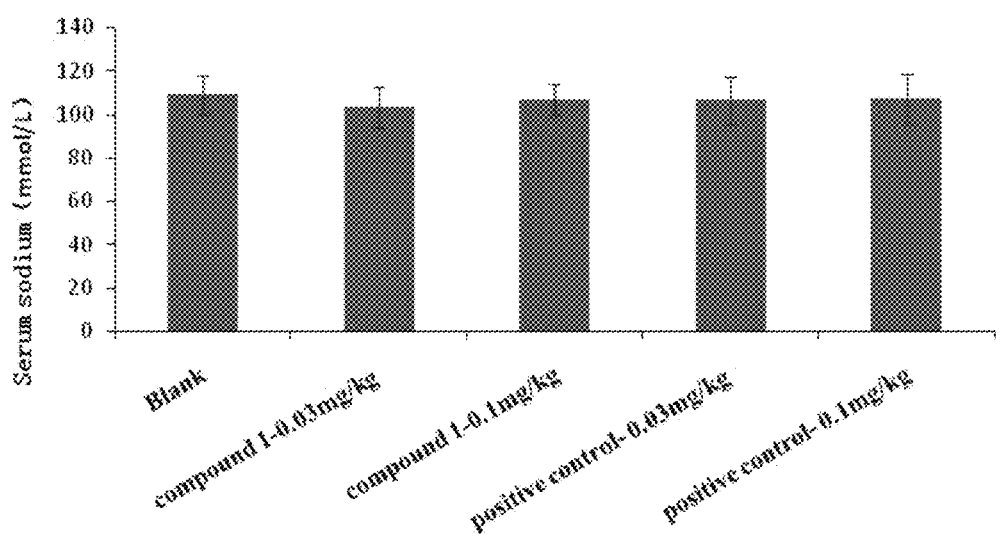
FIG. 4 shows the effect of a ROMK inhibitor on serum sodium of SD rats.
Figure 5:
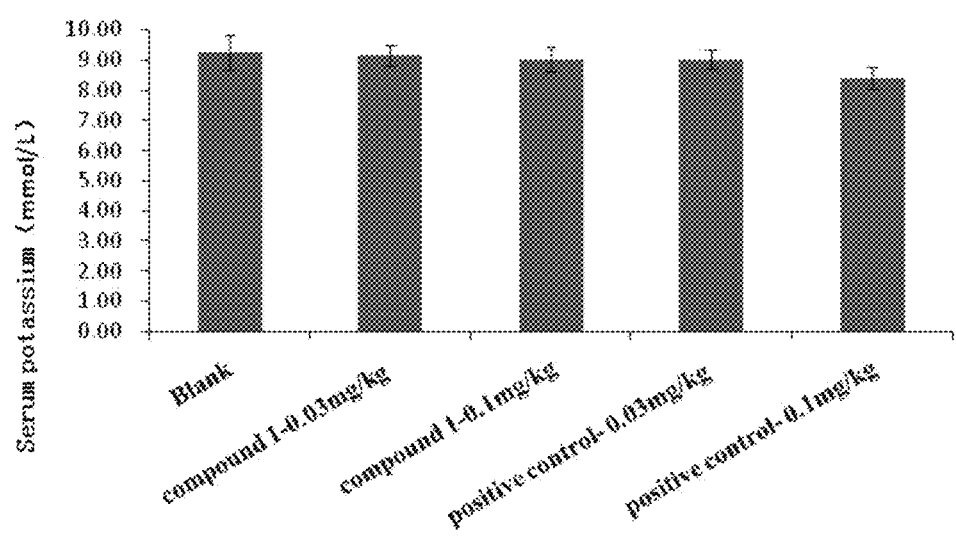
FIG. 5 shows the effect of a ROMK inhibitor on serum potassium of SD rats.

The results show that compared with the blank control group, the urine volume for the positive control drug 0.03 mg/kg and 0.1 mg/kg group increased significantly (P<0.05), in which the urine output was increased 1.41 times and 1.46 times, respectively; the urine volume for compound 1 tested drug 0.03 mg/kg group and 0.1 mg/kg group increased significantly (P<0.01), in which the urinary output was increased by 2.76 times and 3.22 times (see FIG. 1). The positive control drug and the compound 1 group significantly increased urinary sodium excretion (P<0.01), in which the urinary sodium excretion was increased 1.57 times, 1.65 times, 3.12 times and 3.31 times (see FIG. 2). Compared with the normal control group, the urinary potassium for the positive control drug and test drug were slightly elevated, but not statistically significant (see FIG. 3). Simultaneously, the serum sodium and potassium for the positive control drug and each test groups were changed a little (P>0.05) (see FIGS. 4 and 5).

4. Discussion

According to the functional character, K+ channels can be divided into the following four types: slow (delay) K+ channels (K channels), fast (early) K+ channels (A channels), Ca2+ activated K+ channels (K (Ca) channels)) and inwardly rectifying K+ channels. The inwardly rectifying K+ channels (Kir) can be further divided into seven types: Kir1 to Kir7, with different KCNJ encoding genes. The renal outer medullary potassium channel (ROMK) belongs to the Kir1 type. There are at least three subtypes of ROMK in rat kidney: ROMK1, ROMK2 and ROMK3. ROMK2 mostly distributes in the thick segment of the medullary loop ascending branch. ROMK1 and ROMK3 are mainly expressed in the collecting tubules.

The ROMK expressed in the thick segment of the medullary loop ascending branch regulates the secretion and reabsorption of potassium together with Na/K/Cl transporters. The ROMK expressed in the cortical collecting tubules regulates the secretion of potassium together with Na/K transporters. Blocking the ROMK site can promote the secretion of NaCl to the lumen without excessive hypokalemia leading to hypokalemia. It is a good research direction of diuretics for hypertensive patients. This experiment is to explore the diuretic effect of ROMK inhibitors.

In this experiment, the solubility of the test compound 1 was very good. There was no delamination phenomenon. However, when weighing the positive control drug, there was static electricity, which was not easy to weigh, in the initial grinding, there was clumping and poor solubility. After fully grinding, the solubility improved. The results also show that a single oral administration of compound 1 and positive control drug to rats achieves a significant diuretic and sodium excretion effect compared with the normal group. Moreover, the effect was dose-dependent for each dose of the test compound 1 and the positive control drug.

5. Conclusion

Compound 1 and the positive control drug both have significant diuretic and sodium excretion effects, but have no effect on serum potassium. However, the diuretic effect of compound 1 is better than that of the positive control drug. The drug efficacy of each group is dose-dependent.

The invention claimed is:

1. A compound of formula (II),

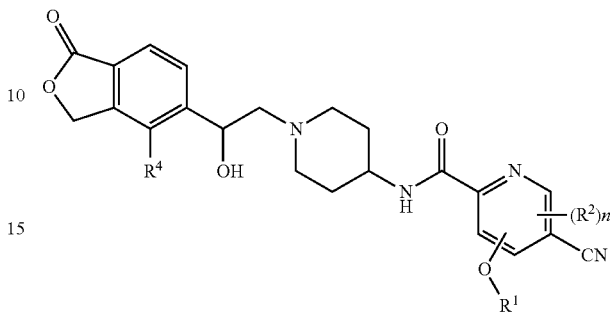

(II)

or a tautomer, mesomer, racemate, enantiomer, diastereomer, or mixture thereof, or pharmaceutically acceptable salt thereof, wherein $R^1$ is alkyl, wherein the alkyl is optionally further substituted by one or more groups selected from the group consisting of halogen, hydroxyl, alkoxy, cycloalkyl, aryl, and carboxyl;

$R^2$ is hydrogen;

$R^4$ is selected from the group consisting of hydrogen, alkyl, halogen, cyano, nitro, alkoxy, cycloalkyl, and aryl;

and n is 2.

2. The compound of formula (II) according to claim 1, wherein $R^1$ is alkyl, wherein the alkyl is optionally further substituted by one or more groups selected from the group consisting of halogen, hydroxyl and alkoxy.

3. The compound of formula (II) according to claim 1, wherein $R^4$ is alkyl.

4. The compound of formula (II) according to claim 1, which is a compound of formula (III):

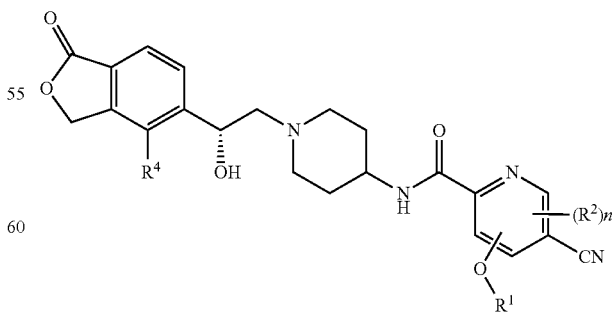

(III)

or pharmaceutically acceptable salt thereof, wherein $R^1$, $R^2$, $R^4$ and n are as defined in claim 1.

5. A compound selected from the group consisting of:

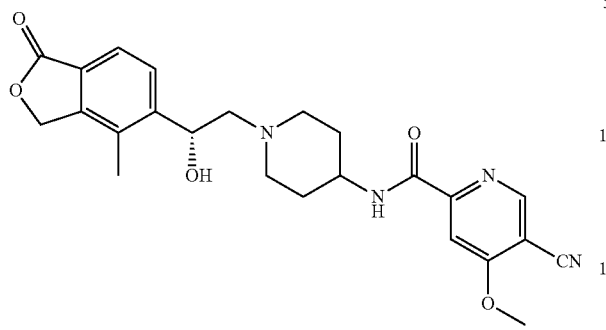

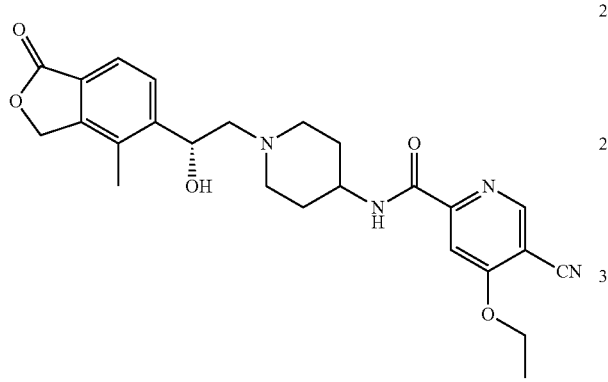

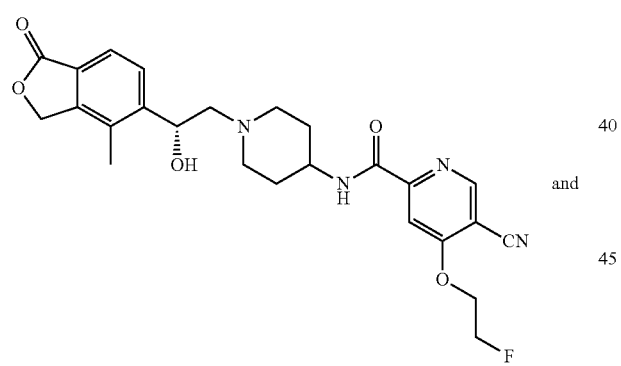

and

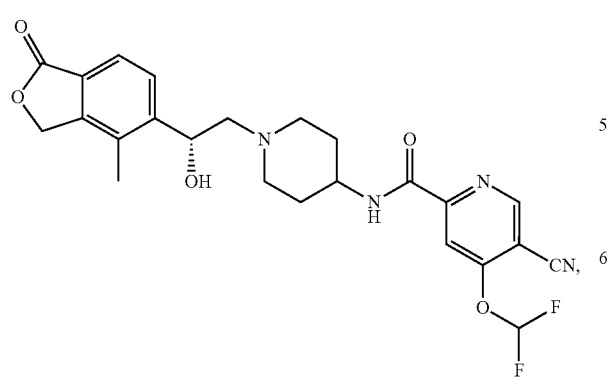

or a pharmaceutically acceptable salt thereof.

6. A pharmaceutical composition comprising a therapeutically effective amount of the compound of formula (II) according to claim 1, and a pharmaceutically acceptable carrier, diluent or excipient.

7. The compound of formula (II) according to claim 2, wherein $R^1$ is selected from the group consisting of methyl, ethyl and propyl.

8. A pharmaceutical composition comprising a therapeutically effective amount of the compound according to claim 5, and a pharmaceutically acceptable carrier, diluent or excipient.

9. The compound according to claim 5, wherein the compound is:

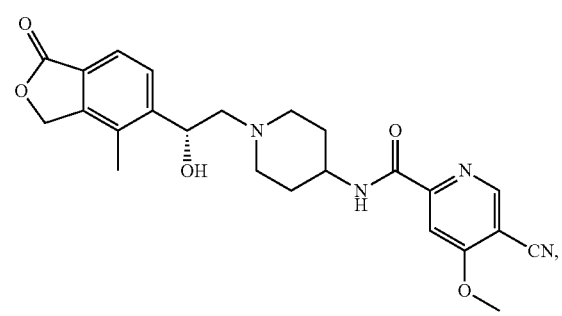

or a pharmaceutically acceptable salt thereof.

10. The compound according to claim 5, wherein the compound is:

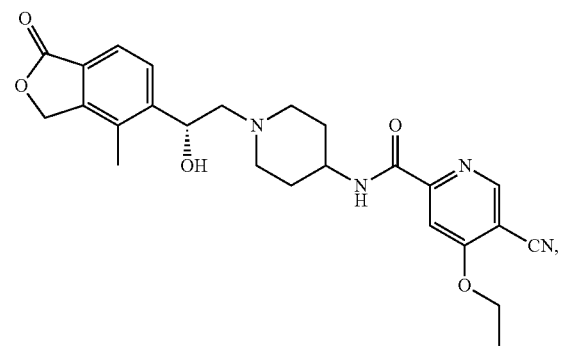

or a pharmaceutically acceptable salt thereof.

11. The compound according to claim 5, wherein the compound is:

47
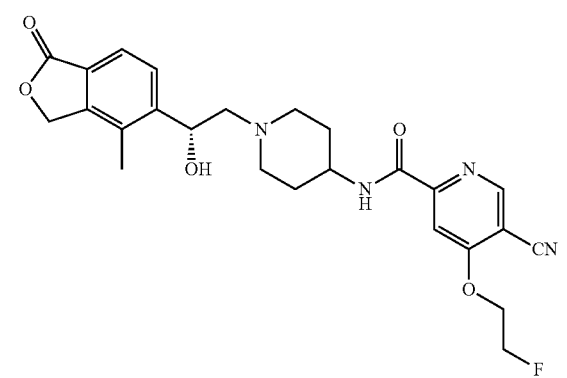
3
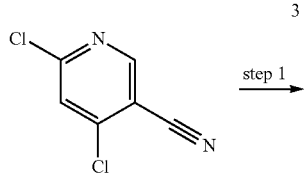
2a
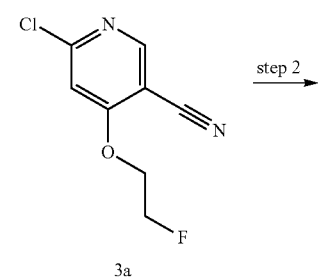
3a
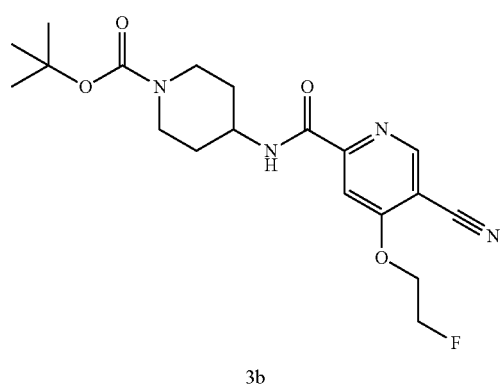
3b
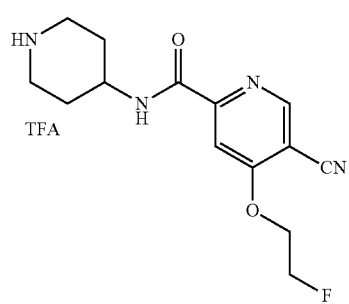
3c
48
-continued
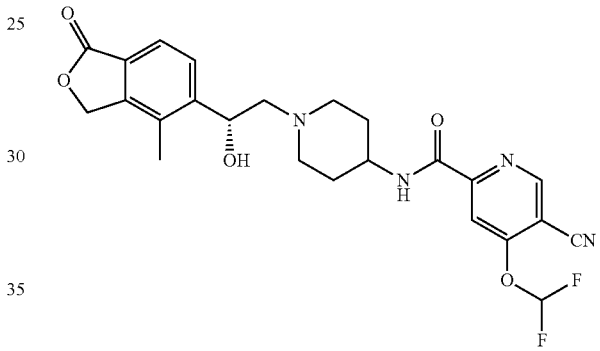
3
or a pharmaceutically acceptable salt thereof.
12. The compound according to claim 5, wherein the compound is:
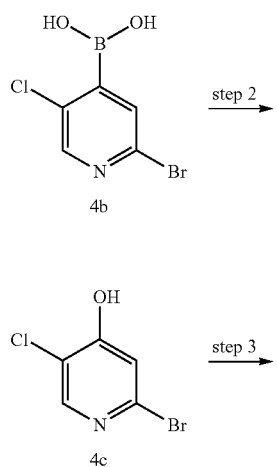
4

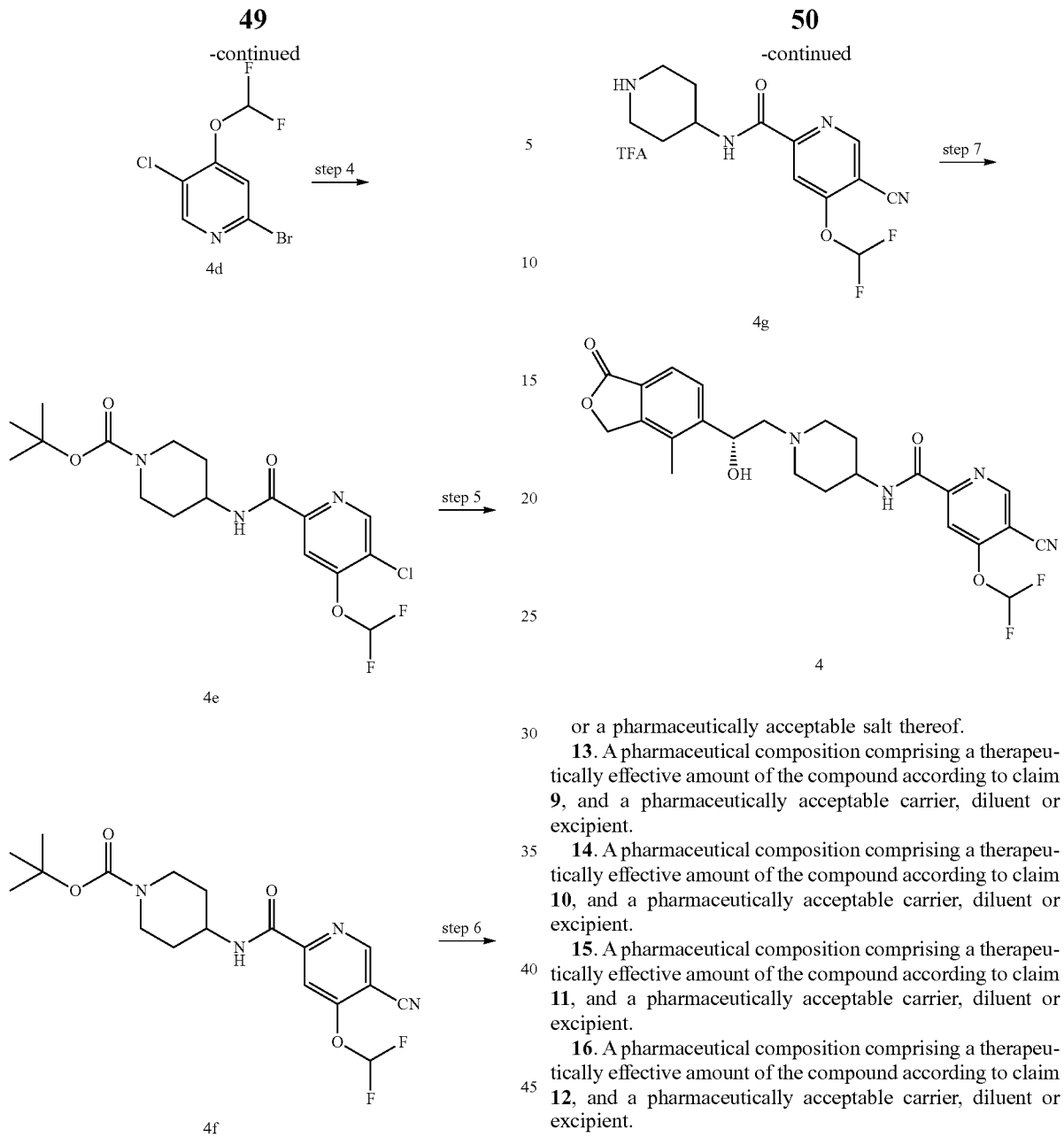

or a pharmaceutically acceptable salt thereof.

13. A pharmaceutical composition comprising a therapeutically effective amount of the compound according to claim 9, and a pharmaceutically acceptable carrier, diluent or excipient.

14. A pharmaceutical composition comprising a therapeutically effective amount of the compound according to claim 10, and a pharmaceutically acceptable carrier, diluent or excipient.

15. A pharmaceutical composition comprising a therapeutically effective amount of the compound according to claim 11, and a pharmaceutically acceptable carrier, diluent or excipient.

16. A pharmaceutical composition comprising a therapeutically effective amount of the compound according to claim 12, and a pharmaceutically acceptable carrier, diluent or excipient.

* * * * *